United States Patent
Porges et al.

(10) Patent No.: US 10,004,410 B2
(45) Date of Patent: Jun. 26, 2018

(54) SYSTEM AND METHODS FOR MEASURING PHYSIOLOGICAL PARAMETERS

(71) Applicants: The Board of Trustees of the University of Illinois, Urbana, IL (US); The University of North Carolina at Chapel Hill, Chapel Hill, NC (US)

(72) Inventors: Stephen W. Porges, Chapel Hill, NC (US); Maria I. Davila, Carrboro, NC (US); Gregory F. Lewis, Cary, NC (US)

(73) Assignees: The Board of Trustees of the University of Illinois, Urbana, IL (US); The University of North Carolina at Chapel Hill, Chapel Hill, NC (US)

( * ) Notice: Subject to any disclaimer, the term of this patent is extended or adjusted under 35 U.S.C. 154(b) by 0 days. days.

(21) Appl. No.: 15/105,674

(22) PCT Filed: Dec. 19, 2014

(86) PCT No.: PCT/US2014/071602
§ 371 (c)(1),
(2) Date: Jun. 17, 2016

(87) PCT Pub. No.: WO2015/095790
PCT Pub. Date: Jun. 25, 2015

(65) Prior Publication Data
US 2016/0317041 A1    Nov. 3, 2016

Related U.S. Application Data

(60) Provisional application No. 61/918,459, filed on Dec. 19, 2013.

(51) Int. Cl.
*A61B 5/0205* (2006.01)
*A61B 5/024* (2006.01)
(Continued)

(52) U.S. Cl.
CPC .............. *A61B 5/024* (2013.01); *A61B 5/002* (2013.01); *A61B 5/0037* (2013.01);
(Continued)

(58) Field of Classification Search
CPC ....... A61B 5/1455; A61B 5/02; A61B 5/0205; A61B 5/026; A61B 5/103; A61B 5/0037;
(Continued)

(56) References Cited

U.S. PATENT DOCUMENTS 5,974,338 A * 10/1999 Asano ................ A61B 5/14535
600/322
6,993,378 B2 * 1/2006 Wiederhold ....... A61B 5/02055
382/115
(Continued)

FOREIGN PATENT DOCUMENTS

WO    WO 2013027027 A2 *   2/2013    ........... A61B 5/0205

*Primary Examiner* — Kennedy Schaetzle
(74) *Attorney, Agent, or Firm* — Valauskas Corder LLC

(57) ABSTRACT

The present invention relates generally to a system and methods for measuring physiological parameters. More specifically, the present invention relates to a noncontact technology by which one or more physiological parameters of a subject may be efficiently and quickly detected. Among other advantages, the present invention can be used to assess and monitor vital signs of one or more subjects in a variety of contexts including for medical or security triage purposes, for use in healthcare waiting rooms, as part of human imaging systems, or during surgery.

23 Claims, 17 Drawing Sheets

(51) Int. Cl.
  *A61B 5/00* (2006.01)
  *A61B 5/08* (2006.01)
  *A61B 5/1455* (2006.01)

(52) U.S. Cl.
  CPC ........ *A61B 5/0077* (2013.01); *A61B 5/02405* (2013.01); *A61B 5/08* (2013.01); *A61B 5/14552* (2013.01); *A61B 5/7235* (2013.01); *A61B 2576/00* (2013.01)

(58) Field of Classification Search
  CPC ... A61B 5/0059; A61B 5/0064; A61B 5/1477; A61B 5/0077; A61B 5/14552; A61B 5/024; A61B 2576/00
  See application file for complete search history.

(56) References Cited

U.S. PATENT DOCUMENTS

| | | | |
|---|---|---|---|
| 8,888,701 B2* | 11/2014 | LeBoeuf | G06F 19/3406 600/301 |
| 9,615,749 B2* | 4/2017 | Clifton | A61B 5/0205 |
| 2003/0002722 A1* | 1/2003 | Jay | A61B 5/0059 382/128 |
| 2008/0038204 A1* | 2/2008 | Yang | A61B 5/0059 424/9.6 |
| 2011/0251493 A1* | 10/2011 | Poh | G06K 9/00255 600/477 |
| 2011/0274338 A1* | 11/2011 | Park | G06K 9/6284 382/133 |
| 2012/0262485 A1* | 10/2012 | Raghoebardajal | G06F 3/011 345/633 |
| 2013/0137949 A1* | 5/2013 | Freeman | A61B 5/0059 600/328 |
| 2013/0271591 A1* | 10/2013 | Van Leest | A61B 5/0064 348/77 |
| 2014/0206965 A1* | 7/2014 | De Haan | A61B 5/7207 600/323 |
| 2014/0303454 A1* | 10/2014 | Clifton | A61B 5/0205 600/301 |
| 2015/0359459 A1* | 12/2015 | Taylor | A61B 5/1034 600/477 |

\* cited by examiner

Camera Sensor Parameter Optimization 900

| Parameter | Default Parameters | Optimal Parameters |
|---|---|---|
| Geometric Mask | | |
| Histogram for Red and Green | | |
| Arterial Pulse | | |

| Camera Control | Shutter | White Balance | Gain | Gamma | Saturation |
|---|---|---|---|---|---|
| Value Range | 28 - 4095 | 0 - 1023 | 48 - 720 | 512 - 4095 | 0 - 4095 |
| Default Settings | 500 | 400 | 100 | 2000 | 2000 |
| Example: Settings optimized for pulse extraction in one context | 350 | 324 | 57 | 2054 | 3058 |

FIG. 9

Pixel Level Pre-processing

Example of (Red, Green, Blue) Pixel Values from a portion of the image

In this example, represented as 8-bit integers

| (10,20,40) | (50,50,50) | (60,62,64) |
| (14,28,120) | (100,120,126) | (80,82,90) |
| (2,24,76) | (46,54,89) | (220,200,211) |

Pixels Excluded in Previous Step — 1001

(Red)
| (10) | (50) | (60) |
| (14) | (100) | (80) |
| (2) | (46) | (220) |

(Green)
| (20) | (50) | (62) |
| (28) | (120) | (82) |
| (24) | (54) | (200) |

(Value)
| (40) | (50) | (64) |
| (120) | (126) | (90) |
| (76) | (89) | (220) |

(Pre-Processed Pixel Values) — 1002

$$5 + \log_{10}\left\{2 + \begin{bmatrix} (10-20)/40 & (50-50)/50 & (60-62)/64 \\ (14-28)/120 & (100-120)/126 & (80-82)/90 \\ & (46-54)/89 & \end{bmatrix}\right\} = \begin{bmatrix} 5.352 & 5.301 & 5.308 \\ 5.326 & 5.334 & 5.306 \\ & 5.320 & \end{bmatrix}$$

FIG. 10

SYSTEM AND METHODS FOR MEASURING PHYSIOLOGICAL PARAMETERS

CROSS REFERENCE TO RELATED PATENTS

This application claims the benefit of U.S. Provisional Application No. 61/918,459, filed Dec. 19, 2013, which is incorporated by reference in its entirety.

FIELD OF INVENTION

The present invention relates generally to a system and methods for measuring physiological parameters. More specifically, the present invention relates to a noncontact technology by which one or more physiological parameters of a subject may be efficiently and quickly detected. Among other advantages, the present invention can be used to assess and monitor vital signs of one or more subjects in a variety of contexts including for medical or security triage purposes, for use in healthcare waiting rooms, as part of human imaging systems, or during surgery.

BACKGROUND OF THE INVENTION

Information regarding the physiological parameters of a subject is important in a variety of contexts and applications, including for healthcare, military, sports, education, adaptive learning, and personal fitness purposes. For example, in psychophysiological research, it is known that the arterial pulse amplitude and rate and respiration of a subject can vary according to the behavioral, emotional, and cognitive challenges presented to the subject. In clinical settings, the condition of a patient may be determined by the measurement of beat-to-beat indices of rate and amplitude of the arterial pulse and breath-to-breath indices of respiration. In intelligence, security, and law enforcement communities, information regarding the physiological parameters of a subject may be useful to achieve a variety of goals.

A variety of devices and methods have been developed by which the physiological parameters of a subject, such as a human subject, can be measured. One such well known group of such devices requires direct contact with the subject in order to obtain the desired information. For example, the stethoscope is an acoustic medical device that is applied to the body of a subject for auscultation purposes, that is, listening to the lung and heart sounds, to the sound of intestines, to the flow of blood in arteries and veins, and other internal sounds of the subject's body. The stethoscope may be used with a sphygmomanometer, another device that is applied to the body of the subject and is commonly used for measurements of blood pressure. Another device, a pulse oximeter is configured to be placed on the fingertips or earlobes of a subject in order to monitor pulse and hemoglobin oxygenation levels. The pulse or heart rate of a subject can be detected and monitored with the use of an electrocardiography ("ECG") device. Such devices detect and amplify the electrical changes that the beating heart produces on the skin of the subject through the use of electrodes affixed to the skin of the subject to which has been applied a gel.

Besides having to be applied to the body of the subject in order to obtain the desired information, there are a variety of other limitations associated with such known measurement devices and methods. One is that in all cases the subject must be located within a distance of the device so that at least the probe portion of it can be applied to the body of the subject. Another is that certain known devices require that some material be applied to the body of the subject before contact of the probe with the body is made. For example, with an ECG device, gel must be applied to the body of the subject before the electrodes are affixed to the body. A material such as this gel may cause irritation of the skin of the subject. Such known systems and methods may provide also a limited range of information that is often qualitative, may be inconvenient for both the subject and the operator, and by their use the physiological parameter(s) that are being measured may be affected.

Other devices have been developed for the estimation and monitoring of a subject's heart rate which do not require contact with the subject's skin. These non-contact devices are based on the recognition that the beat of the heart sends a pulse wave through the subject's body. The wave produces slight changes in the blood vessels beneath the skin of the subject. The small changes in the blood vessels can produce changes in the light that is reflected from the skin. By obtaining a color image of the skin of the subject, and analyzing the images for changes in light reflectance, the pulse of the subject can be determined. Devices that estimate the pulse of a subject based on the light reflected from the skin of the subject typically do so by taking a sequence of multiple images of the subject and collectively analyzing and comparing the entire group of images to obtain an estimation of the subject's heart rate.

Many known non-contact heart rate estimations/monitoring systems and methods have a number of limitations associated with them. One is that they typically require that images be captured of a subject over a period of time. The need to capture such a series of related images adds to the amount of time that is needed in order to conduct and complete the analysis of interest and make a determination regarding the heart rate of the subject. The subject may move or the lighting of the subject may change during the period in which the images are captured. Such changes in the subject and the context in which the images of the subject are taken add to the complexity of the processing needed to obtain the information that is sought. Also, as the number of images that are taken increases, the amount of data that must be gathered, recorded and processed in order to make the determination increases. For example, if a video recording is taken of a subject for 60 seconds at 60 frames per second, and each of the frames has a region of 300 by 300 pixels, with separate data collected for certain colors—for example, red, green, and blue—the data integer values equals 972 million. Expanded resources are needed to receive and record this amount of data. Handling and processing this amount of data is time consuming and increases the chance that error will occur.

Accordingly, there exists a need for a noncontact technology capable of detecting human physiological parameters that provides accurate information, is quick and efficient, and convenient to use for both operator and the subject. The present invention satisfies the demand.

BRIEF SUMMARY OF THE INVENTION

The present invention provides a system and methods for measuring the physiological parameters of one or more subjects. Embodiments of the present invention include a system and methods by which the physiological parameters of the subject may be measured by the analysis of one or more digital images captured of a subject. More specifically, certain embodiments of the present invention may include a device for capturing one or more digital images of a subject. The present invention utilizes the captured images in order to indirectly measure the volumetric changes of the arterial tree in the subcutaneous layer of human skin, via changes of the light reflected by the skin. The arterial pulse can be identified by determining the extent to which the light reflected by the skin changes from frame to frame. The arterial pulse information obtained with the present invention is an indirect measure of the volume of blood in the arteries and arterioles present in the dermis and subcutaneous layer of the skin. The device may include one or more imaging sensor components by which one or more bands of the light spectrum captured through the lens of the capture device may be separated to provide separate light data such as in one or more "layers".

Certain embodiments of the present invention may include also a "pre-processing component" by which at least a "Region of Interest" ("ROI")—that is the portion of the image that may likely provide information that is particularly relevant to the physiological parameter that is the target of the investigation—to be identified in the image. The pre-processing component may be configured in order to receive and process the digital output from the one or more imaging sensor components in order to analyze the pixels in a single captured image frame to facilitate the identification of the ROI. For example, in order to determine the pulse of a subject, the portion of the captured image in which the skin on the face of the subject appears may be considered to be a candidate for the source of the ROI. The pre-processing component of the system may be configured to identify the facial skin portion appearing in the captured image by, for example, a multi-step process.

One embodiment of such a pre-processing component includes a multi-step process having at least two steps—a first exclusionary step in which it is determined which pixels of the captured image are likely to provide information useful to determine the ROI and thereby assist in determining the target physiological parameter and a second correction step in which information from one or more sensors—for example, the red pixels produced by a red light sensor or the calculated color planes, such as the hue value for each pixel—may be used to further refine the information within the defined ROI to ultimately allow the target physiological parameter to be assessed.

The first exclusionary step may "pre-process" the pixels of the captured image in order to separate them based upon the pixel level values of, for example, several color components (e.g., Hue, Saturation, and Luminance) of each of the pixels from which the captured image is formed. In certain embodiments of the present invention, the pre-processing component is configurable in order to provide additional information by which the ROI can be identified. For example, if the ROI is the skin of a subject's face, an edge of glasses that the subject may be wearing or the facial hair of the subject may be identified by searching the image pixels for those that form the shadow developed by the frame of the glasses or for the local texture that hair forms and those pixels associated with these non-skin features excluded from further analysis. Such operation of the first exclusionary step can produce in effect a "binary", "Yes/No" mask" for each pixel of the image and thereby the entire captured image and generate what is termed for purposes of this application an "analysis pixel set".

The second correction step may process the analysis pixel set to correct for local differences in, for example, luminance, proximity to one or more edges (e.g., the edges of a pair of glasses), and contextual information (e.g., orientation with regard to light direction) and use the information from the one or more light sensors which may be used to capture the image. For example, in order to identify the pulse of a subject, pixels containing red sensor information and pixels containing green sensor information would be sought in the correction processing step. One reason for such a processing configuration in which the color blue is excluded is that a primary contributor to the blue color is melanin, which varies with skin color. Mean values of green and red are less affected by differences in skin color across subjects. Contextual information may include that by which a particular feature of the subject—for example, a nostril or a vein—may be identified and made useful for purposes of determining the target physiological parameter. This second correction step provides what is termed for purposes of this application a "pre-processed analysis pixel set".

In one embodiment of the invention, the pixels from a captured image may be pre-processed by separating the light captured from the ROI into the red, green, and blue ("RGB") color components and the red and green components analyzed to calculate their mean values by a histogram function while the blue color component is excluded from such analysis. In certain embodiments of the present invention, the mean values of the green and red color components of the ROI for each image may be divided to create a common mode rejection ratio that cancels common signals not related to arterial pulse, including, for example, movement by the subject, shifts in light, and camera artifacts.

In another embodiment of the invention, an additional pre-processing step calculates new values for each pixel by combining information from separate color planes in a correction step that yields a set of Pre-Processed Analysis Pixels. In this embodiment, only a portion of the "Pre-Processed Analysis Set" values may convey physiological information. The selection of this "Final Analysis Subset" of these "Pre-processed Analysis Pixels" may then be used to calculate a pulse sample from the image.

In both embodiments mentioned in the previous two paragraphs, the resulting signal—designated for purposes of this application as Raw Video Pulse—may convey arterial pulse and respiration information for a particular time point. Additional signal processing of the Raw Video Pulse signal may be conducted to separate the signals that describe cardiac and respiratory activities, thus generating a clean arterial pulse wave. In certain embodiments, the pulse signal may be generated by 2nd order Butterworth bandpass (0.5 Hz-2.5 Hz) filtering of the Raw Video Pulse signals.

Embodiments of the present invention pre-process each frame that is captured separately and, after each such processing is complete, the resultant data is compared to determine the physiological parameter. Such individual processing reduces the overall amount of information that must be assessed at one time and ultimately may speed up the process of assessing the physiological parameter. By using a single frame to obtain information from which the signal can be determined, the present invention provides a nearly "real-time" system to assess and monitor the physiological parameters of one or more subjects. This is in contrast to known non-contact systems that, for example, require the time consuming capture and analysis of a sequence of images before information regarding the physiological parameter of a subject may be provided to a user.

Certain embodiments of the present invention can be configured to provide information regarding physiological signals that are not measurable in the visible light spectrum. For example, an embodiment of the present invention that includes a capture device having an infrared light sensor can be used to produce pixels in which the intensity value of the pixel will vary according to the thermal changes that appear in the subject. Advantageously, such an embodiment permits the respiratory rate of a subject to be determined by examining the thermal intensity of the small number of pixels around the edge of the nostrils of a subject.

Additional embodiments of the present invention can be configured to provide information regarding physiological signals that are measurable in both the visible light spectrum and at least a portion of the non-visible light spectrum. For example, one embodiment of the present invention can include one or more sensors for color in the visible spectrum in order, for example, to determine the heart rate of a subject and a sensor in the infrared range in order, for example, to determine the temperature of the subject. Advantageously, such an embodiment may allow a subject having an infection to be identified in a crowd of subjects.

Certain embodiments of the present invention follow what is termed a "D1-to-A-to-D2" extraction protocol in which "D1" represents the digital output obtained from the capture device and the one or more sensors associated with it, "A" represents the analog signal reconstruction of the target physiological parameter that results from the pre-processing of the captured information, and "D2" represents the digital representation of the specific features of the physiological signal (for example, the duration between heart beats, the amplitude of the pulse wave, etc.) that is communicated to the user. The analog signal may be constructed from D1 through use of interpolation models informed by the physiology of the signal being monitored.

In certain embodiments, the number of pixels used to define the captured images may be adjusted to define the amount of data that needs to be processed and the accuracy of the estimation that is obtained.

Through the use of the present invention, interbeat intervals (IBI), two components of heart rate variability (HRV) (low frequency (LF), and respiratory sinus arrhythmia (RSA)), breathing rate (BR), and arterial pulse amplitude on a beat-to-beat basis may be measured.

An advantage of the system and methods for measuring physiological parameters is that physiological parameters are measured without making contact with the body.

Another advantage of the system and methods for measuring physiological parameters is that images captured through a video recording may be used to provide the desired information.

An additional advantage of the system and methods for measuring physiological parameters is that results may be provided in real time through the analysis of separate captured images and the comparison of the results of each analysis.

An added advantage of the present invention is that results may be obtained without the need to store large amounts of data and without massive computation of large data sets.

A further advantage of the system and methods for measuring physiological parameters is certain embodiments may be configured such that only a single set (one red value and one green value) of measurements is required to generate one sample in the pulse wave.

Another advantage of the system and methods is that one or more steps of the present invention may be implemented through software-based embodiments or hardware-based embodiments. Yet another advantage of the system and methods for measuring physiological parameters is that is a low cost, easy to use option.

Another advantage of the system and methods for measuring physiological parameters is that it can be used without the production of any material that is typically considered to be a biohazard.

Additional objects, advantages and novel features of the examples will be set forth in part in the description which follows, and in part will become apparent to those skilled in the art upon examination of the following description and the accompanying drawings or may be learned by production or operation of the examples. The objects and advantages of the concepts may be realized and attained by means of the methodologies, instrumentalities and combinations particularly pointed out in the appended claims.

BRIEF DESCRIPTION OF THE DRAWINGS

The figures depict one or more implementations in accord with the present concepts, by way of example only, not by way of limitation. In the figures, like reference numerals refer to the same or similar elements.

FIG. 9 illustrates an exemplary embodiment of the process directed to data acquisition according to the present invention.

FIG. 10 illustrates an exemplary embodiment of a pre-processing component according to the present invention.

DETAILED DESCRIPTION OF THE INVENTION

The present invention includes a system 21 by which various methods may be practiced for the assessment and monitoring of one or more physiological parameters. The system 21 includes an image capture device 31, a processing component 41, and a display component 51 by which the information obtained through the use of the processing component 41 can be communicated to the user.

Figure 1:
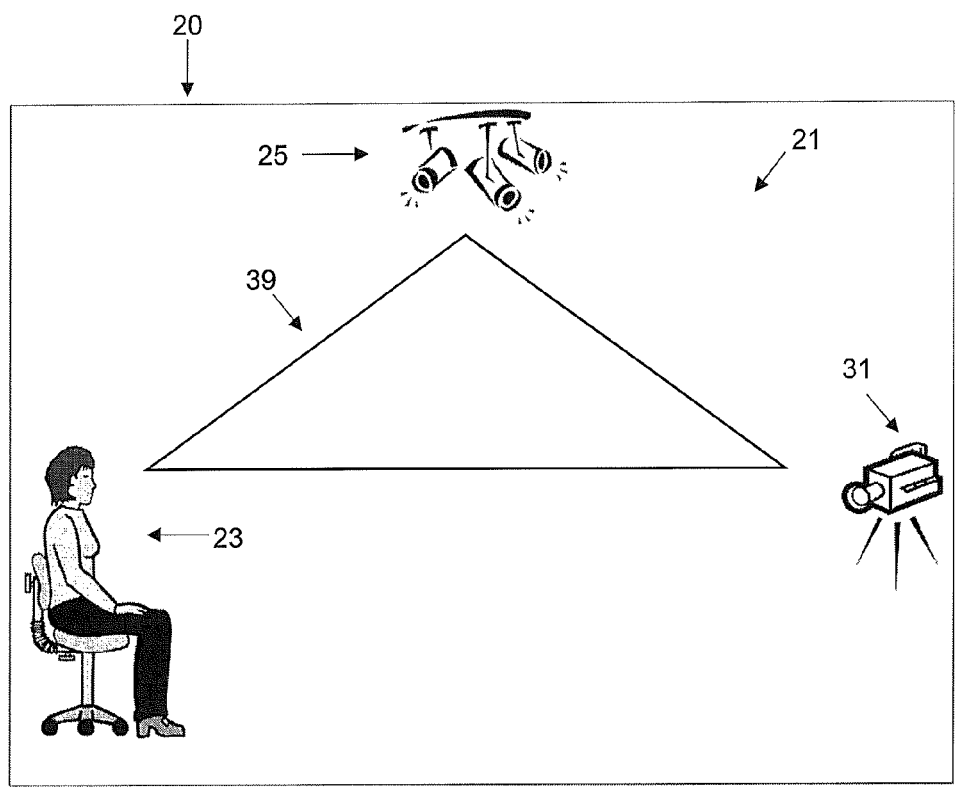
FIG. 1 illustrates an exemplary embodiment of the present invention showing the use of the capture device relative to a seated subject.

FIG. 1 illustrates an exemplary embodiment 20 showing one context in which the system 21 may be used. The context shows a subject 23 having a position such that one or more images of the subject 23 may be captured by the capture device 31. The context may be lighted by natural light (daylight ambient light), one or more sources of artificial light 25, or a combination of both. The artificial light source 25 may have bulbs, tubes, or similar means (not shown) by which a spectrum of light may be produced. The artificial light source 25 may be configured to produce a spectrum of light that is visible to humans, not visible to humans, or a combination of both in line with the goals of the user of the system 21.

The capture device 31 may be one in which images may be obtained. The capture device 31 may be a digital camera that is able to capture rapidly a series of related images to produce the illusion of movement (that is, a "movie" or a "video"). Associated with the capture device may be a local and/or remote memory component (not shown) by which the captured images may be stored at least until the processing of the images is begun. The capture device 31 may be configured to capture images in one or more particular portions of the spectrum or multiple spectra through the use of one or more lenses, filters, or sensors (not shown).

One embodiment of the capture device 31 may be a commercial digital color video camera that includes a charge-coupled device (CCD) sensor, a complementary metal-oxide-semiconductor (CMOS) sensor, or other light sensor. The capture device 31 may measure the segment of light in the visible band, that is, the portion of the electromagnetic spectrum in the region from 380 to 775 nm approximately. Certain embodiments of the capture device 31 may measure light not in the visible band or a combination of both visible and invisible.

The light captured by the device may be segmented using a Bayer filter pattern into three sub bands: blue band (380 to 500 nm), green band (500 to 600 nm), and red band (600 to 775 nm). The skin optical properties and the digital color capabilities of the capture device 31 may enable the system 21 to function, for example, as a biosensor to measure human biological activity through the analysis of information obtained from the surface of the subject in real time.

The relationship between the light (whether natural, artificial, or a mixture of both) and the subject 23 illuminated by it, and the images that are captured by the capture device 31 is diagrammatically emphasized by the triangular shape 39 juxtaposed in FIG. 1. By changing the lighting, the position of the subject, and the configuration of the capture device 31, the images that may be captured and processed according to the present invention and the information developed from same may be changed.

In the context shown in FIG. 1, the artificial light source 25 is positioned to illuminate at least the face of the subject 23. Typically, light penetrates the skin of a subject to a depth of about 2-3 mm. A certain percentage of the light is absorbed by the epidermis. Depending on the skin color, some of the light is transmitted through the epidermis and reaches the dermis where the different components of the dermis reflect, absorb and/or transmit the light. The main source of absorptance and reflectance in the dermis and subcutaneous layer of the skin is the hemoglobin present in the blood vessels. The volume of blood in the arteries and arterioles changes as a function of the beating of the heart. Each heartbeat generates a pressure wave that changes the radius of arteries and arterioles. Volumetric changes in the arterial bed are translated into reflectance and absorptance changes of the incident light. The capture device 31 captures the light present in the room. When the device 31 is focused on the face of the subject 23, it captures the subtle changes of light emitted by the face due to beating of the subject's heart. When there is more blood in the arteries and arterioles and more light is absorbed by the blood, the device 31 senses less reflected light. On the contrary when there is less blood in the arteries and arterioles and less light is absorbed by the blood, the device 31 senses more reflected light.

The arterial pulse information obtained with the system 21 is an indirect measure of the volume of blood in the arteries and arterioles present in the dermis and subcutaneous layer of the skin. The device 31 is configurable to detect the arterial pulse by the change in light from frame to frame of the captured images. Images of the skin of a seated subject may be captured by the device 31 at specified sampling frequency.

Figure 2:
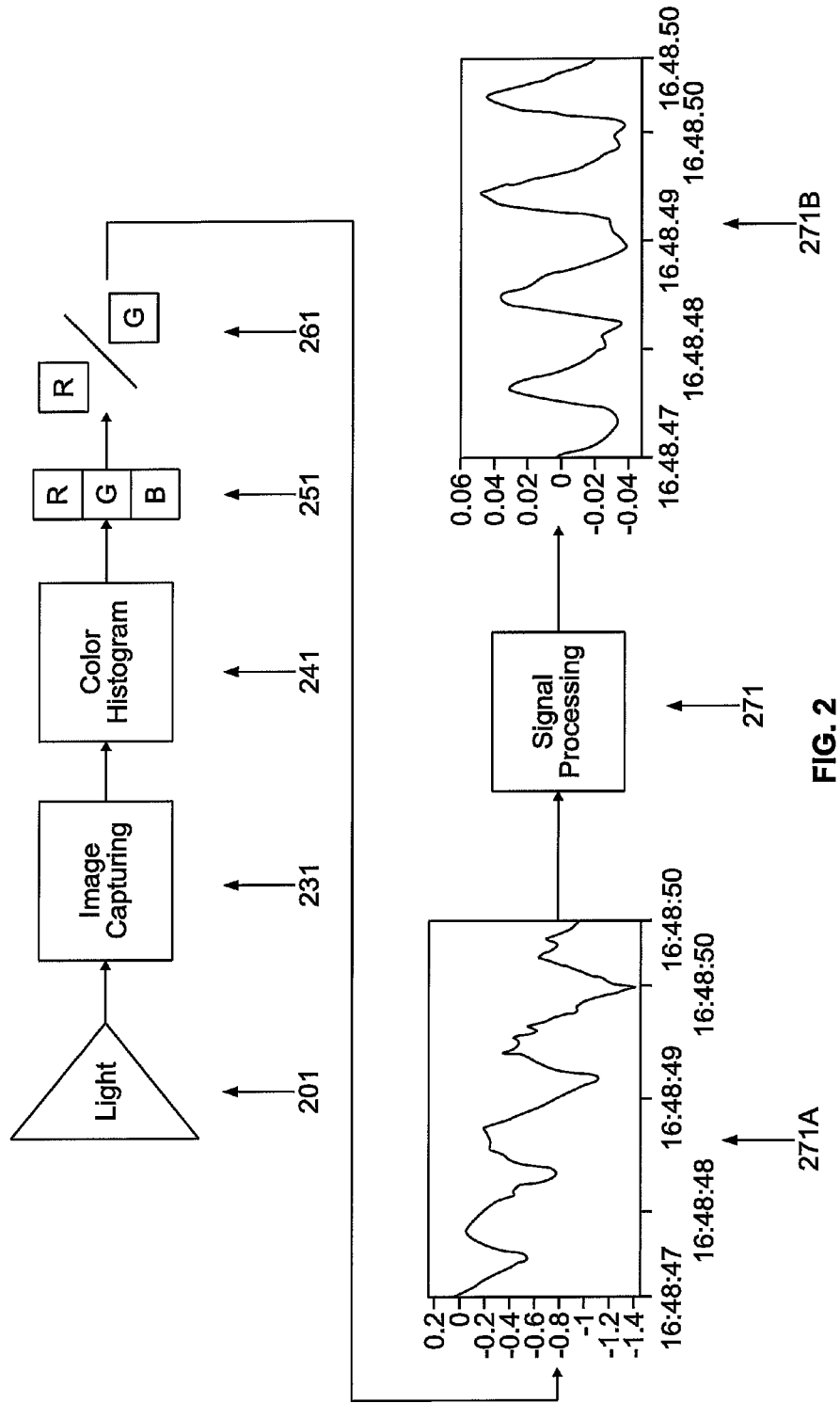
FIG. 2 illustrates a diagram showing the operation of one embodiment of the system according to the present invention by which the one or more physiological parameters of a subject may be determined.

FIG. 2 provides a diagram of the operation of one embodiment of the present invention. The system 21 illustrated in FIG. 2 may be used to identify the arterial pulse of a subject 23. As shown in FIG. 2, the light 201 reflected from the surface of the body of the subject 23 can be sufficient to permit the device 31 to capture of at least one image 231 through the use of a capture device 31 such as a commercial color digital video camera. The capture of the image 231 includes the transformation of the light entering the device 31 by the sensor component of the device 31 into discrete digital data. The number of pixels in the sensor will determine the number of pixels in the recorded image. The embodiment of the system 21 illustrated in FIG. 2 includes a color histogram function component 241 by which the captured light can be processed to produce a red/green/blue output 251. As explained above, the color blue does not provide a reliable source of information for purposes of determining the physiological parameters of a subject and the system 21 includes an exclusionary component 261 by which the blue color is excluded to produce a red/green output 271A. Further processing of the output by a signal processing component 271 can produce data 271B from which an estimation of the arterial pulse wave of the subject 23 can be generated.

Figure 3:
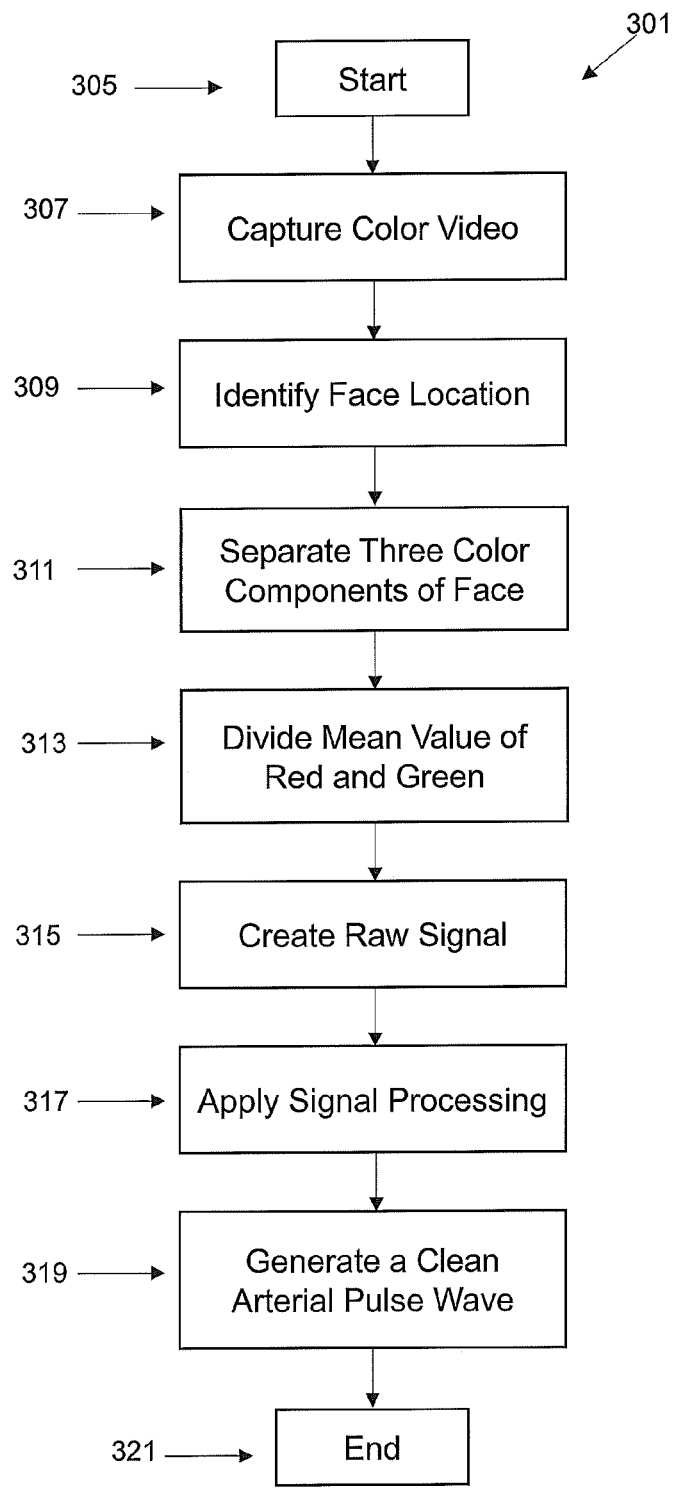
FIG. 3 illustrates an exemplary flow diagram of one embodiment of a non-contact method by which information regarding a subject may be obtained and processed in order to estimate the arterial pulse of a subject.

FIG. 3 illustrates an exemplary flow diagram of one embodiment of a non-contact method 301 by which information regarding a subject may be obtained and processed in order to estimate the arterial pulse of a subject. After the Start 305 of the method 301, a capture device 31—such as a color video camera—may be used to capture one or more images. While more than one image may be captured, certain embodiments of the present invention analyze each captured image separately to provide data by which the one captured image may be compared with the data obtained from one or more other captured images. The first or first few images that are captured may be used to make adjustments to the settings (for example, exposure duration or analog or digital gain) of the capture device in order to provide one or subsequent images that differ from the initial image or images. Through the image or images that are initially captured 307, the ROI to be analyzed is selected or identified. In certain embodiments, the ROI is the face or a portion of the face of a subject 23. However, it is contemplated that any surface of the body of a subject may provide information useful to determine one or more physiological parameters of a subject 23. For certain purposes, the surface may include any part of the body of the subject 23 with a high capillary density. In further embodiment, it is also contemplated that this approach may be used on surfaces of organs. For example, if the surface of the brain of a subject 23 was exposed, and the capture device 31 was used to visualize this surface, the method 301 may also be used.

The method 301 includes the step of separating the selected ROI into the RGB color components 311. Mean values of red and green color components may be calculated by a software component—such as a histogram function—or hardware.

In one embodiment, mean values of the green and red color are divided to create a common mode rejection ratio 313 by which what are estimated to be common signals not related to arterial pulse (e.g. subject's subtle movement, light shifts, and camera artifacts) may be cancelled). The resulting raw signal 315 is developed and is identified for purposes of this application "Raw Video Pulse". Additional signal processing of the Raw Video Pulse signal may be performed 317 to separate the signals that describe cardiac and respiratory activities. Finally, a clean arterial pulse wave may be generated 319.

Figure 5:
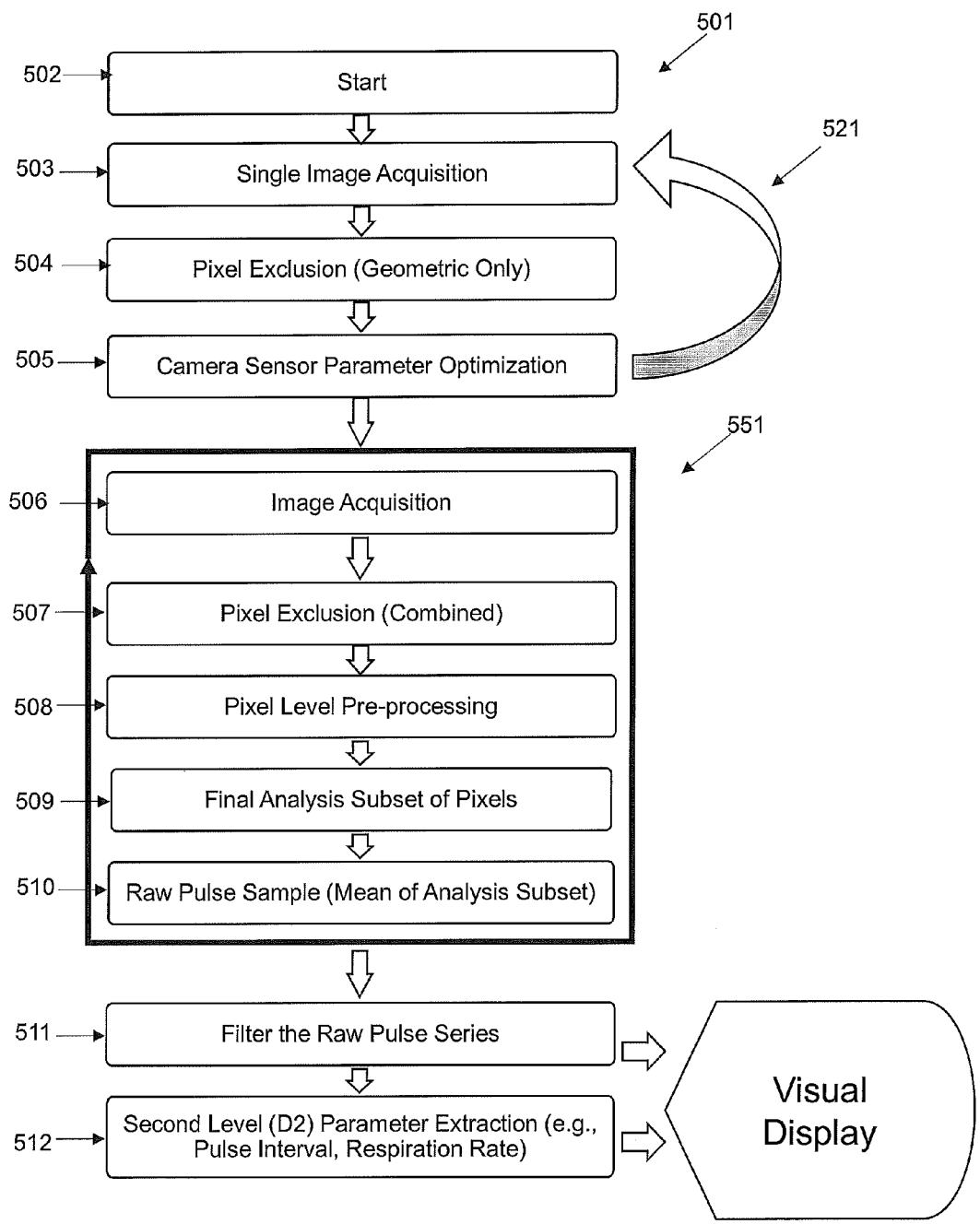
FIG. 5 illustrates an exemplary flow diagram of obtaining and processing data in accordance with another embodiment of the present invention.

FIG. 5 illustrates an exemplary flow diagram of one embodiment of a non-contact method 501 that includes optimizing the sensor settings of the capture device 31 based on a single image of the subject 23 with additional processing directed to each frame 551 in order to estimate the arterial pulse of a subject. After the Start 502 of the method 501, a capture device 31—such as a color video camera— may be used to capture one image 503. The ROI to be analyzed is selected or identified 504. In certain embodiments, the ROI is the face or a portion of the face of a subject 23. This distribution of Red and Green pixel values, which convey the pulse information independent of skin color, within the ROI of this image is used to inform adjustments, either manual or automated, to the digital sensor settings 505 (e.g., exposure duration, analog or digital gain, white balance) to maximize the information content of the subsequent images captured.

In the FIG. 5 illustrated embodiment, after the adjustments are made, an additional image may be captured 521 and the distribution of Red and Green pixel values inspected within the ROI defined by the geometric mask 600, again by manual or automated processes and adjustments further made to the sensor settings. This process of capturing and analyzing an additional image continues until the optimal camera sensor parameters are achieved for the current subject 23 in the current environment 39. All subsequent acquired frames 551 may then be processed by the method illustrated in FIG. 4. As with respect to the FIG. 3 embodiment, in certain embodiments, the ROI is the face or a portion of the face of a subject 23. However, it is contemplated that any surface of the body of a subject may provide information useful to determine one or more physiological parameters of a subject 23. For certain purposes, the surface may include any part of the body of the subject 23 with a high capillary density. In further embodiment, it is also contemplated that this approach may be used on surfaces of organs. For example, if the surface of the brain of a subject 23 was exposed, and the capture device 31 may visualize this surface, the method 501 may also be used.

Figure 4:
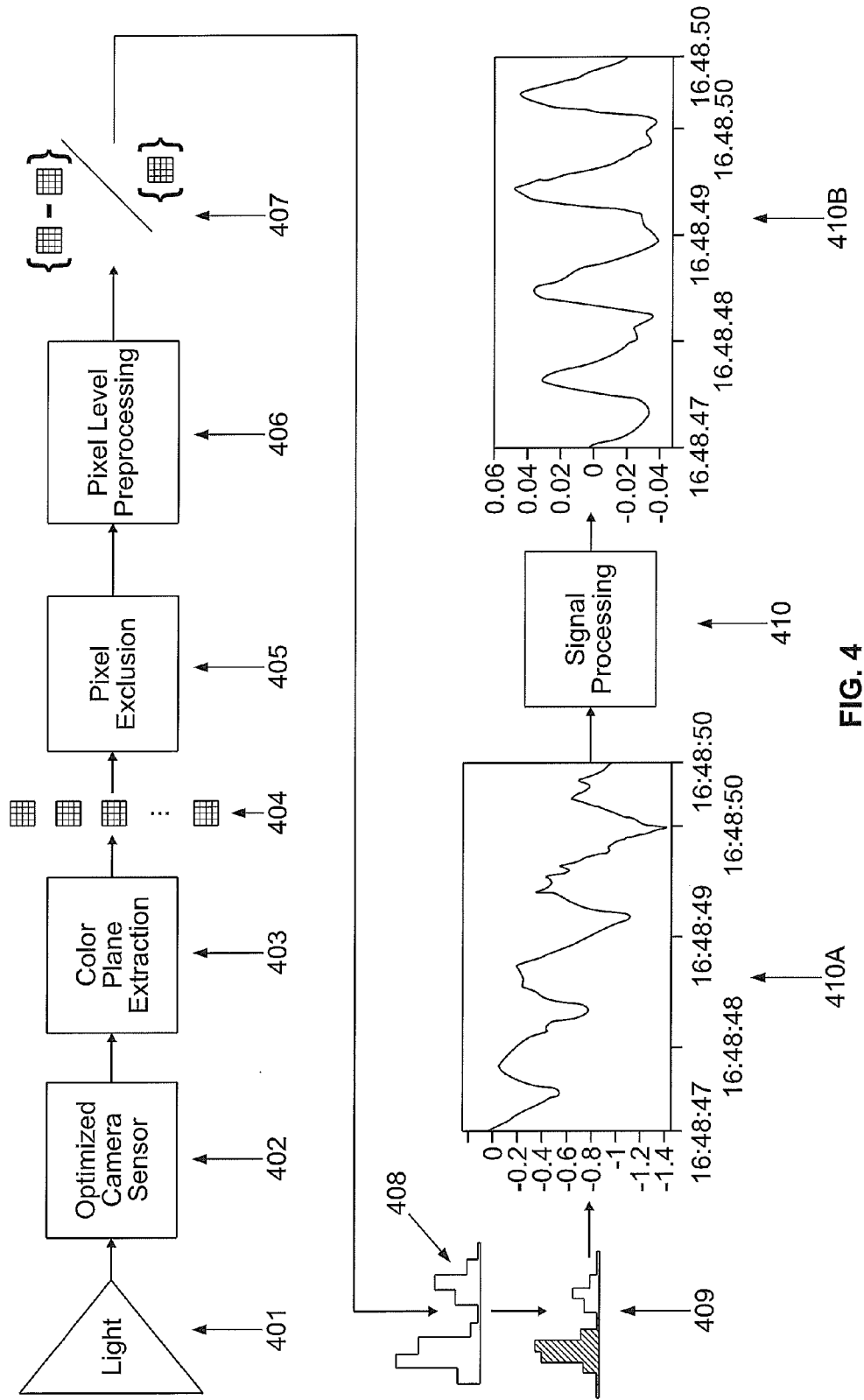
FIG. 4 illustrates a diagram showing the operation of another embodiment of the system according to the present invention by which one or more physiological parameters of a subject may be determined.

FIG. 4 diagram of the operation of one embodiment of the present invention. The processing 551 includes the step of extracting the color planes from the acquiring a single frame 402, extracting the individual color sensor component planes 403 (e.g., Red, Green and Blue) and deriving the additional color planes (e.g., Hue, Saturation, Luminance, Value and Intensity) to generate a set of color planes 404 (e.g., Red, Green, Value, etc.) that all have the same number of pixels as the original image 402. Pixels are then excluded from further processing by the combination 800 of a geometric mask 600 and skin mask 700. Accepted pixels are then pre-processed by mathematical combinations 407 of two or more of the extracted color planes 404 to generate an array of pre-processed pixel values the same size as the original pixel array 402. In one embodiment, the mathematical operation is defined by the formula 1002:

$$\text{Preprocessed Pixel Value} = 5 + \text{Log}_{10}(2 + [\text{Red} - \text{Green}]/[\text{Value}])$$

However other embodiments may use other combinations (e.g., [Green]/[Luminance]) of color planes to complete the pixel level preprocessing 406. These combinations of information may be generated by any of the standard mathematical operations. In these examples, with coordinates in a frame given by [x,y] and the operation carried out across the full set { } of coordinates in the image, (e.g., addition {preprocessed value[1,1]=Red[1,1]+Luminance[1,1]}, division {preprocessed value[4,3]=Red[4,3]/Green[4,3]}, multiplication {preprocessed value[120,140]=Green[120,140]*Red[120,140]*Luminance[120,140]}), depending upon the signal of interest and the selected sensor. The combination may be across color planes within one pixel as in the examples above, or across pixels within one color plane (e.g., {preprocessed value[1,1]=Red[1,1]−Red[1,2]}, or {preprocessed value[3,4]=Luminance[3,4]/Luminance[4,4]}). The set of pre-processed values is then transformed into a 1D array of values (excluding the excluded pixels) and transformed by a histogram function 408. Two modes are observed in this distribution and the first mode is identified 409. The final analysis subset of pixels 509 is a fixed number of pixels closest to the first mode. In one embodiment, the number of pixels is 3% of the total image acquisition size. The pulse sample for the acquired frame is the mean of these values 510. The sequence of the pulse samples is a Raw Video Pulse signal 410A. Additional signal processing of the Raw Video Pulse is performed 410 to generate a clean arterial pulse wave 410B.

Figure 6:
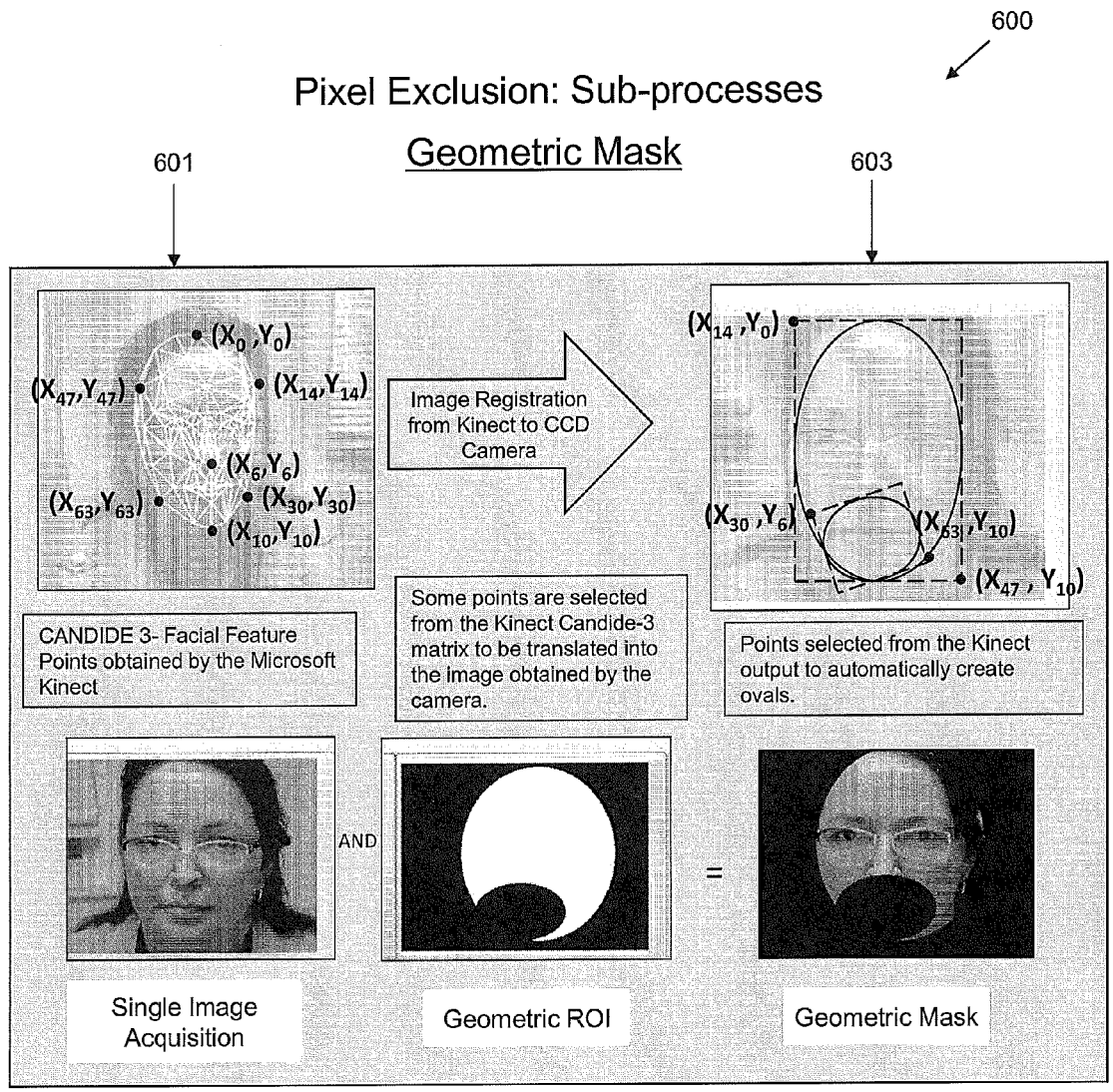
FIG. 6 illustrates an exemplary embodiment of the process by which a component of the present invention may be developed according to the present invention.

FIG. 6 is a diagram illustrating the operation of one embodiment of the present invention by which a geometric mask for the pixels in one frame may be generated. The process 600 includes an identification step 601 in which facial features of a subject 23 are identified. Such an identification step 601 may be carried out by a third party system. The identification system translates the location of a set of facial features to the coordinate system of the imaging sensor 31. One such third party system is the Kinect sensor. The process 600 includes a shape creation step 603 in which the points obtained through the operation of the identification step 601 are applied to an image obtained through the use of the capture device 31. In the illustrated embodiment, the points are used to create oval shapes. In the illustrated embodiment, a Geometric ROI may be developed through the use of the shapes and therefore a Geometric Mask. One region is selected to encompass the face, and another to encompass the mouth area. The face area that is not within the mouth region is defined by a binary mask.

Figure 7:
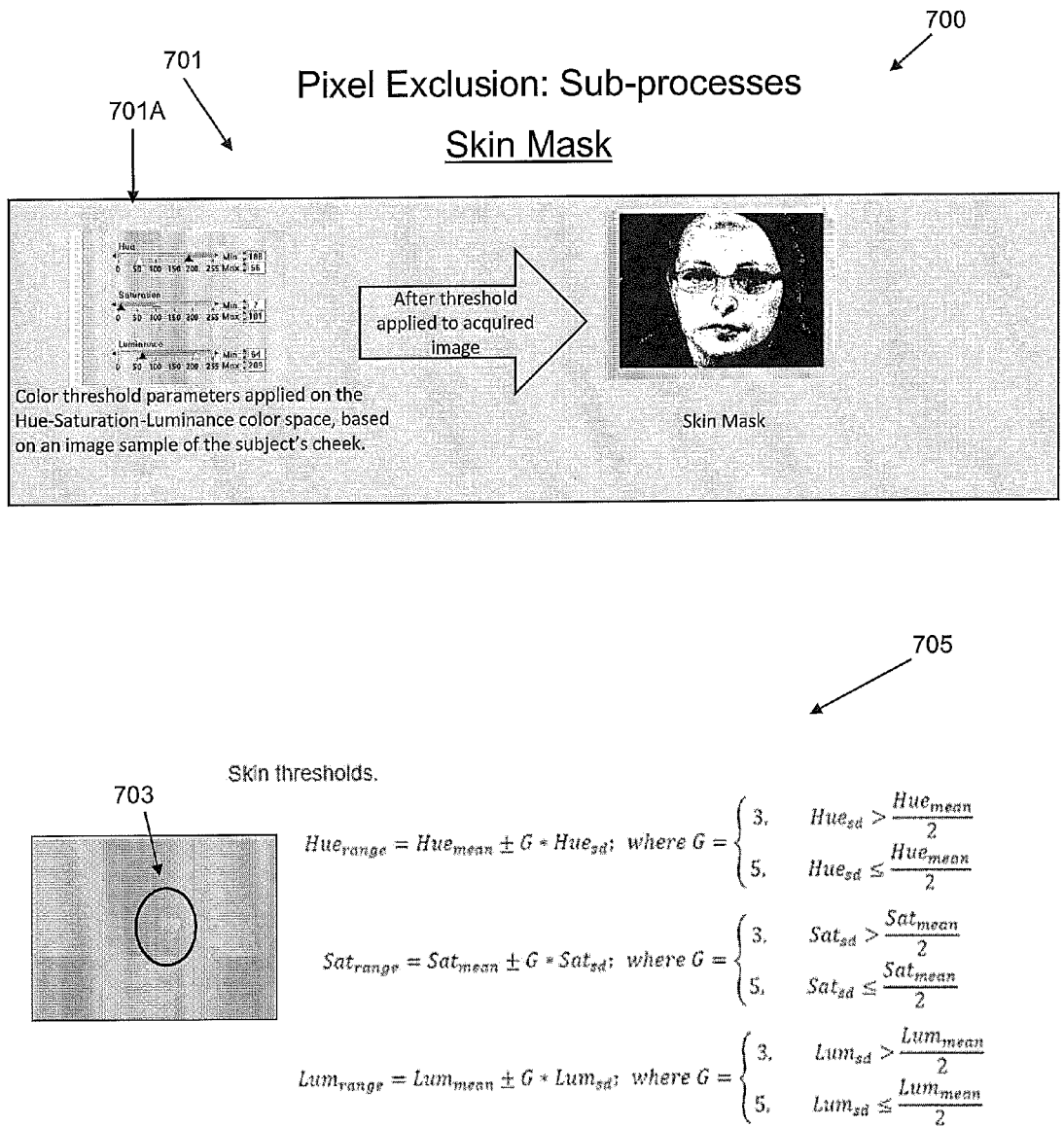
FIG. 7 illustrates an exemplary embodiment of the process by which another component of the present invention may be developed according to the present invention.

FIG. 7 is a diagram that illustrates an embodiment of the process 700 by which a skin color based mask may be developed from the pixels in one image captured by a capture device 31. The embodiment of the process 700 includes a configuration step 701. One embodiment of the configuration step 701 uses a user interface 701A such as the one illustrated in FIG. 7 in which the distribution of Hue, Saturation and Luminance are selected for a small region of the subject 23. The small region used in the illustrated embodiment is a portion of the cheek 703. In one embodiment, the range of acceptable values for each parameter (e.g., Hue) are determined by formulae such as those shown at 705. However, it is contemplated that other formulae may be appropriate in other embodiments of the invention, including for the extraction of other physiological signals.

Figure 8:
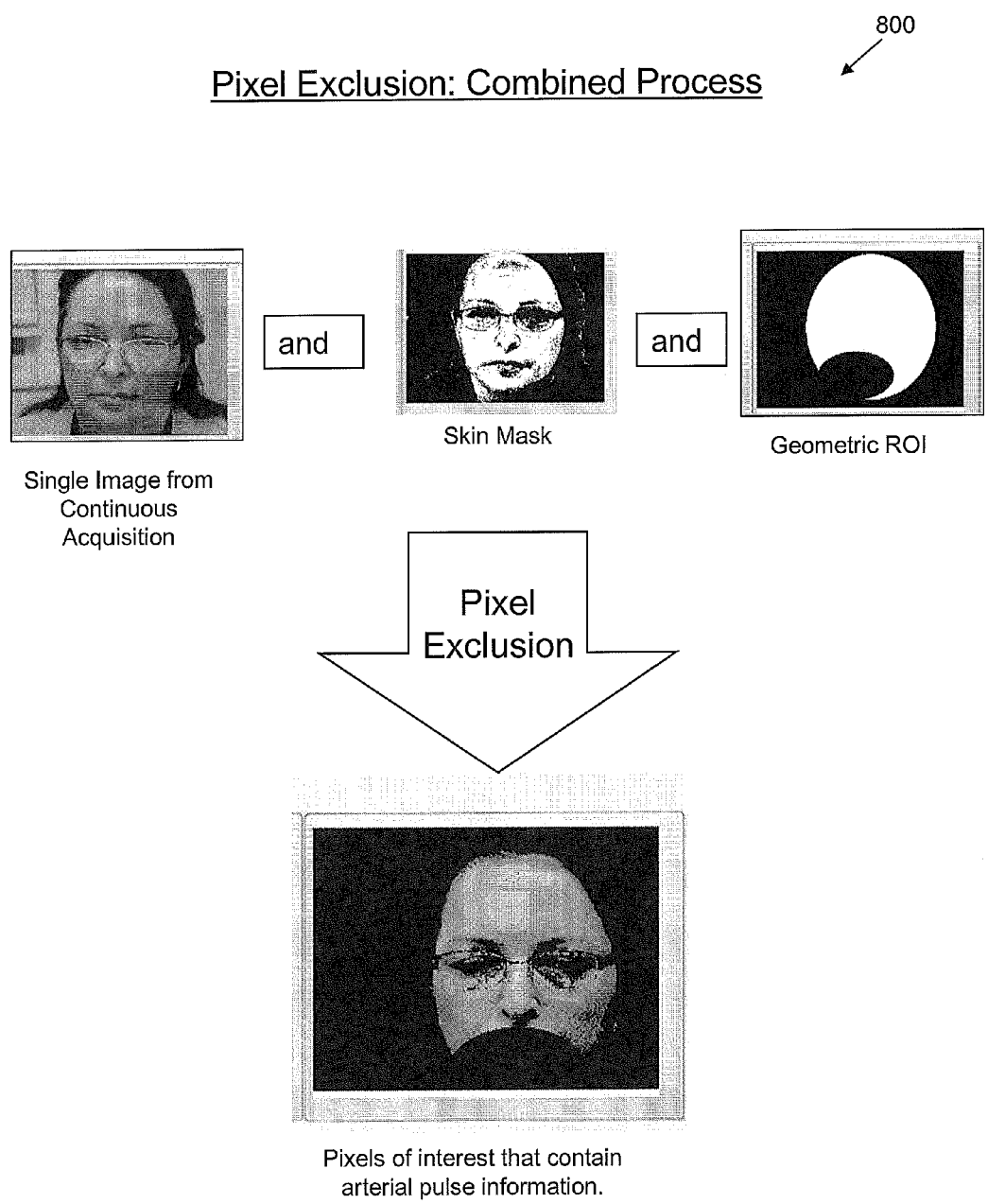
FIG. 8 illustrates an exemplary embodiment of the process by which an additional component of the present invention may be developed according to the present invention.

FIG. 8 is a diagram showing one embodiment of the operation of the exclusionary step. More specifically, the diagram shows the use of an embodiment of the present invention by which the two masks produced through the operation of the processes shown in FIG. 6 and FIG. 7 are used with pixel exclusion to identify the pixels of interest that contain, for example, arterial pulse information. In the illustrated embodiment 800, a skin mask and a geometric ROI are applied to an image captured through the use of the capture device 31. Pixels that are included by both the geometric mask 600 and skin mask 700 are passed unchanged to the color histogram 241 in one embodiment or to the color plane extraction 403 of another embodiment of the invention. The pixels passed out of step 800 represent the "Analysis Pixel Set", and are then further processed to isolate the physiological signal of interest.

FIG. 9 is a diagram of an embodiment of the present invention by which the selection of the capture device sensor parameters (shutter, white balance, gain, gamma, and saturation) may be optimized. The illustrated embodiment may be used to minimize the influence of light changes due to subject movements. The value of the different parameters may be adjusted in response to the illumination conditions in the environment and the skin type of the subject 23. The controls of the capture device 31 may be optimized in a feedback loop, based on the Red and Green histogram of the subject's geometric mask. In another embodiment, changes in the sensor control parameters of the capture device 31 facilitate the extraction of different physiological signals. For example, pulse oxygenation requires longest shutter exposure time. The chart 905 shows settings of the capture device 31 that are optimized for pulse extraction. In contrast, arterial pulse requires shorter shutter exposure time.

FIG. 10 is a diagram illustrating an embodiment of the pixel level pre-processing step 508 in the method 501. The input to step 1000 is the "Analysis Pixel Set" passed from the exclusionary step 800. The pixel level preprocessing 1000 generates a signal that is more robust in separation from noise due to subject movement. In one embodiment, the invention may be used to track heart rate from a user who is operating a piece of exercise equipment. In such an embodiment, the pixel level of preprocessing the frames will be required in order to provide a stable estimate of heart rate. The method 1000 excludes from mathematical combination 1001 any pixels that were rejected by the combined masks in 800. The resulting array of pixel values 1002 may be of a different numeric type than the color plane values, for example, the input arrays in 1000 are 8-bit integer values derived from a Red-Green-Blue sensor, while the output array 1002 is made of double-precision floating point numbers. This array of resulting values comprises the "Pre-Processed Analysis Pixel Set". This correction step is utilized in method 501. It is contemplated that other ranges of pixel values may be obtained by different sensors in other embodiments. For instance, thermal imaging sensors may generate pixel arrays of 32-bit integer values.

Figure 11:
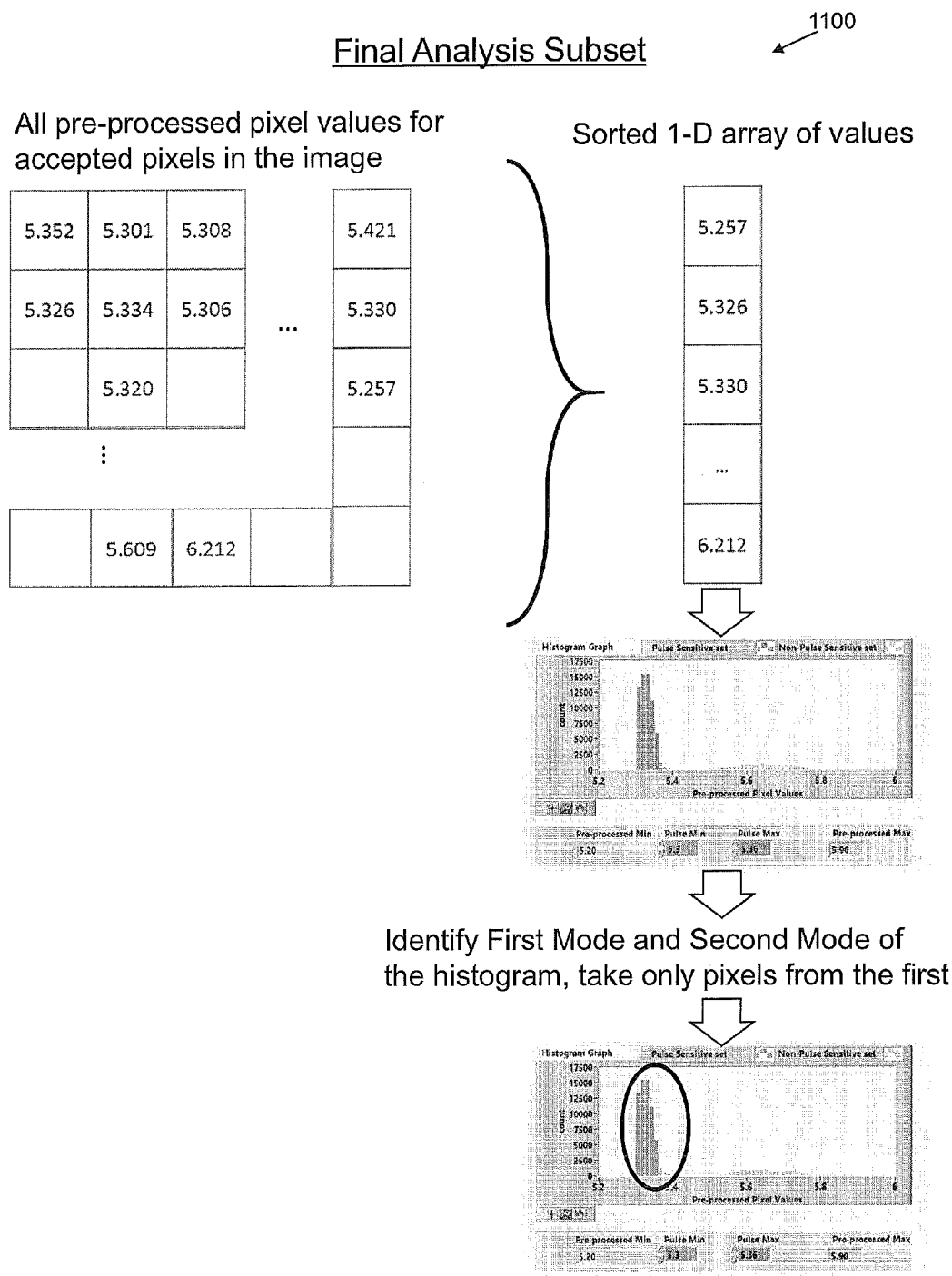
FIG. 11 illustrates an exemplary embodiment showing the processing of data obtained through the use of the present invention.

FIG. 11 is a diagram illustrating an embodiment for the selection of the "Final Analysis Subset" of pixels for one step 506 in the method 501. Through the use of the illustrated embodiment, the two dimensional array of the "Pre-Processed Analysis Pixel Set" values is transformed into a single column array of numbers. Masked pixels that were excluded in step 800 have no value due to the exclusion 1001 and thus are not included in this column. The column is transformed by a histogram function. In the method 501 for pulse extraction the preprocessed values have two modes. Only one mode conveys information about the pulse, and that mode is selected automatically 1100. The values near this mode fluctuate with each pulse wave. "Pre-Processed Pixel Array Set" values associated with other common modes convey only noise, and their exclusion from analysis is a major advantage of the present invention. The relevant mode is identified, and a fixed number of pixels closest to this value are extracted into the "Final Analysis Subset" of Pixels 509. In one embodiment, the number of pixels in 509 is fixed at 3% of the total number of pixels in the acquired image. It is anticipated that this percentage will vary based upon parameters of the subject 23, environment 39, sensor 31 or lighting 25. The mean of these pixel values determines the Raw Pulse Sample 510 for this frame 506.

In certain embodiments, a D1-to-A-to-D2 extraction protocol is employed. The digitized image output from the sensor is transformed, based on the known properties of the underlying physiological process, into an estimate of the 1-Dimensional physiological signal. The algorithm is based upon processing the data in each image (frame by frame), not by comparing or accumulating a sequence of images or their components. The unit of measurement in this approach is a single, two-dimensional (2D) frame of information detected by an imaging sensor.

In order to obtain information regarding certain physiological parameters, such as to determine the cardiac pulse of a subject, the imaging sensor used may be a color sensor with RGB-sensitive pixels or other digital cameras sensitive to visible light. Other embodiments of the capture device 31 may operate in a similar sequence of processes on wavelengths detected outside the visible band. FIG. 5 shows the type of target physiological process that may be detectable through the analysis of what portion of the light spectrum. The capture device 31 can be configured to include one or more sensor components to detect light appropriate for the selected physiological parameter.

Real time monitoring: The D1-to-A-to-D2 approach has particular significance in application, since the signal is 'real-time' or One-In/One-Out, making certain applications feasible (e.g., monitoring a patient) and certain features more robust (e.g., recovering from a loss of the signal).

In certain embodiments, multiple subjects may be monitored with one sensor. Within a busy hospital emergency room, a single capture device 31 may be positioned to monitor the vital signs of more than one person within view of the device. When, for example, a person shows a sudden change in vital signs, for example a rapid pulse, an alarm could trigger, alerting the staff to a medical incident.

In certain embodiments, the present invention may be used to provide biofeedback. For example, in one application, the pulse signal may be monitored, transformed into a beat to beat interval series, analyzed to estimate cardiac vagal tone (i.e., a component of heart rate variability characterized by a periodic process in the beat-to-beat heart rate time series and known as the amplitude of respiratory sinus arrhythmia), and the result is feedback to the user in real-time as a form of biofeedback In certain embodiments, the system and methods of the invention may further include a thermosensor. In one example of this embodiment, a color sensor and a thermal imager are used to simultaneously measure a subject's temperature and heart rate. This embodiment has various applications, including, for example, screening people at a checkpoint for possible infection.

In certain embodiments, system and methods of the invention could be used to continuously monitor the heart rate of a subject while the subject is exercising, for example, on a treadmill. The subject may be able to monitor cardiac output without any wires or need to stop moving or place hands on a sensor to obtain a reliable signal.

Other applications of the system and methods of the invention include, without limitation: oxygen saturation using face or hand and a long exposure time and narrow wavelength band; blood pressure rhythms in pulse wave; mental health screening based on facial muscle tone; and skin absorption changes due to toxins.

In certain embodiments, the quality of the raw data may be improved prior to analysis by reducing or eliminating the contribution of non-skin pixels using masking. In certain embodiments, the hue, saturation, and/or luminance profile of the subject's face is used to design a specific 'skin mask'. This mask is then applied to the incoming frames to refine the ROI, and reduce or eliminate non-skin pixels (e.g., hair, eyes).

In certain embodiments, respiration frequency may be extracted by estimating the frequency of the RSA component in the pulse interval series. Alternatively or additionally, respiration frequency may be extracted by measuring respiration-induced motion, e.g., movement of the shoulders, chest, diaphragm, or by use of the infrared wavelengths detected by the system 21 using a thermal sensor. In certain embodiments, the system and methods of the invention may include motion tracking devices, e.g., commercially available motion tracking devices such as Kinect or eyetracker devices.

In certain embodiments, the system and methods may use stereo vision by including two or more cameras to generate a 3D model of the field of view, e.g., to isolate the subject's head.

In certain embodiments, pixel level correction for illumination of the ROI may be achieved in real-time pre-processing of the frame to generate a sample of the pulse wave using the calculation: mean (red levels/pixel luminance)/mean (green levels/pixel luminance)=sample of pulse wave.

Figure 12:
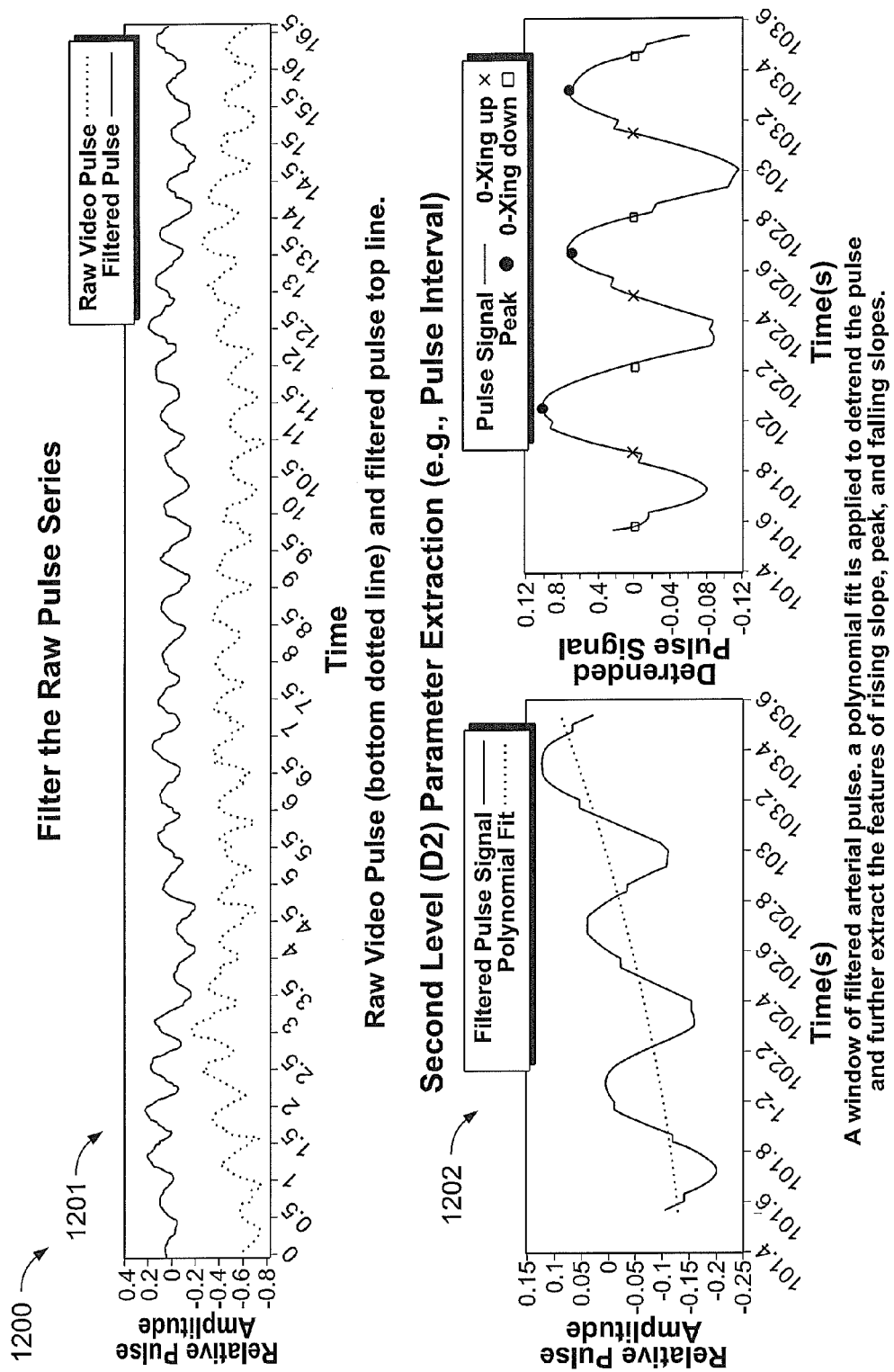
FIG. 12 illustrates exemplary embodiments of the display of information obtained through the use of the present invention.

In certain embodiments, motion correction is achieved by buffering the tracking information and coordinating it with a different frame rate camera. FIG. 12 is a diagram illustrating an embodiment of the signal processing 511 or 317 step in generating the clean pulse wave 319. The raw pulse wave is processed with a Butterworth bandpass filter. In one embodiment the passband is set at 0.2 Hz to 5.0 Hz. In one embodiment a first order derivative is calculated from the filter output 1201. In certain embodiments, multi-parameter pulse detection is used, i.e., three features, including rising zero-crossing/peak/falling zero-crossing 1202. In certain embodiments, multi-parameter pulse detection is used, i.e., three features, including rising zero-crossing/peak/falling zero-crossing 1202.

Figure 13:
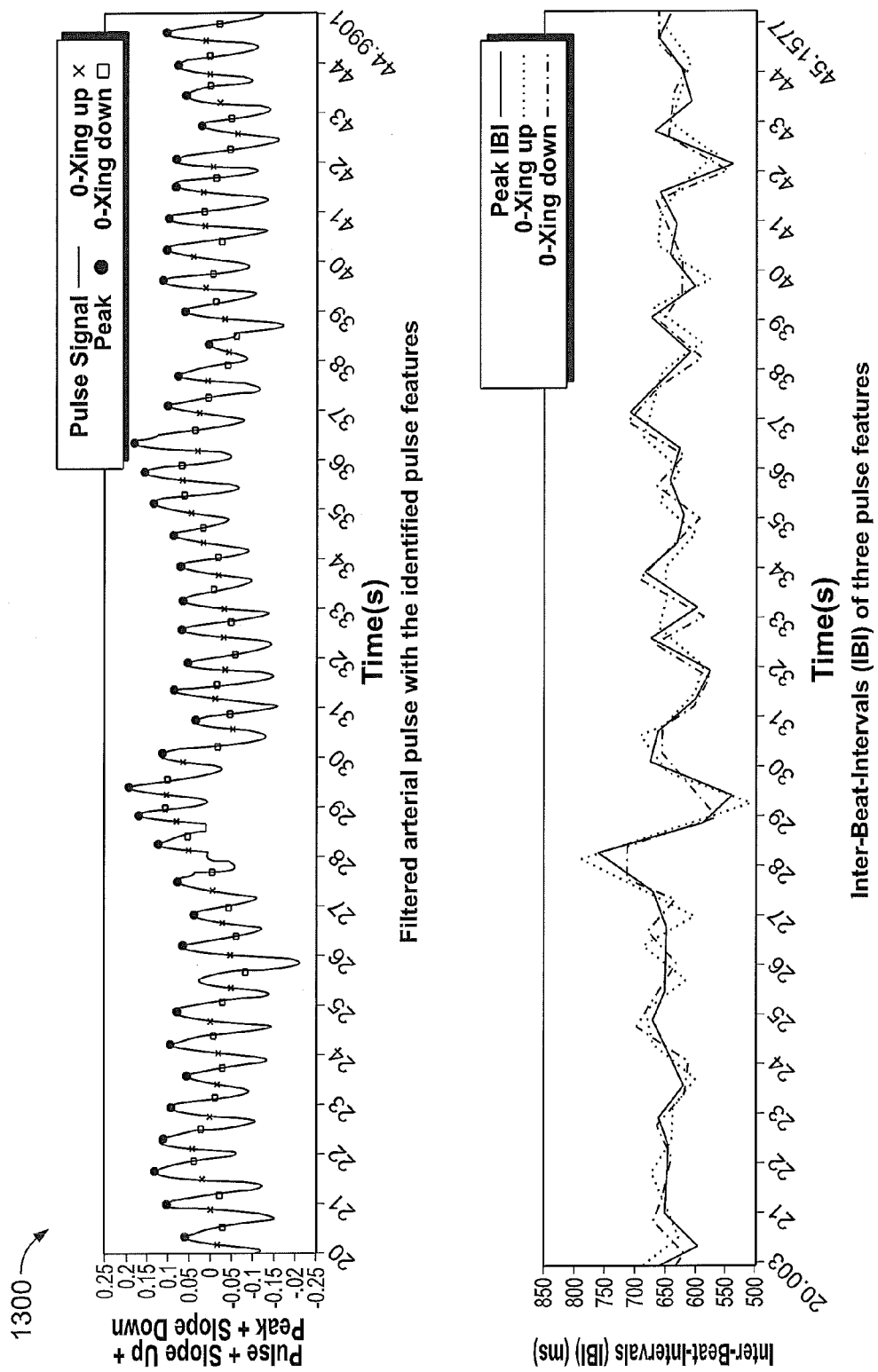
FIG. 13 illustrates other exemplary embodiments of the display of information obtained through the use of the present invention.

FIG. 13 is a diagram illustrating an embodiment of the physiological feature extraction step to generate the variable D2. In one embodiment the feature extracted is the inter-pulse interval time. In 1300 the identified pulse wave features are shown in the top graph, and in the lower graph the pulse intervals between each successive feature are shown over a 25 second period.

In certain embodiments, a Grasshopper® IEEE-1394b (FireWire) digital camera (Point Grey Research Inc., Richmond, BC, Canada) is used or other commercial CCD or CMOS device or light sensor, and color signals with wavelengths between 300 and 800 nanometers are monitored. In certain embodiments, resolution of 640×480 pixels is used and raw 8-bit RGB Bayer data transmitted. In certain embodiment, a sampling rate of ~60 frames per second (fps) for off-line testing or ~30 fps for on-line testing.

In certain embodiment, Viola-Jones (OpenCV) is used for face detection or other face detection algorithm.

In certain embodiments, Lucas-Kanade optical flow (LabVIEW) method is used for face tracking or other face tracking algorithm. In this method, three points on the face are tracked, middle forehead, nose, and chin.

The physiological parameters that may be obtained through the present invention are the interbeat interval (IBI) or instantaneous heart rate, respiratory sinus arrhythmia (RSA) and low frequency (LF) cardiac rhythms and other components of heart rate variability (HRV), pulse amplitude, and respiration or breathing rate (BR). However it is also contemplated that other human physiological parameters may also be obtained. It is also contemplated that further parameters may be detected, such as biological substances or bodily secretions. For example, it is contemplated that the system and method may detect biological substances such as sweat and urine. Additionally, biological secretions and biological excretions may be detected as well.

Figure 14:
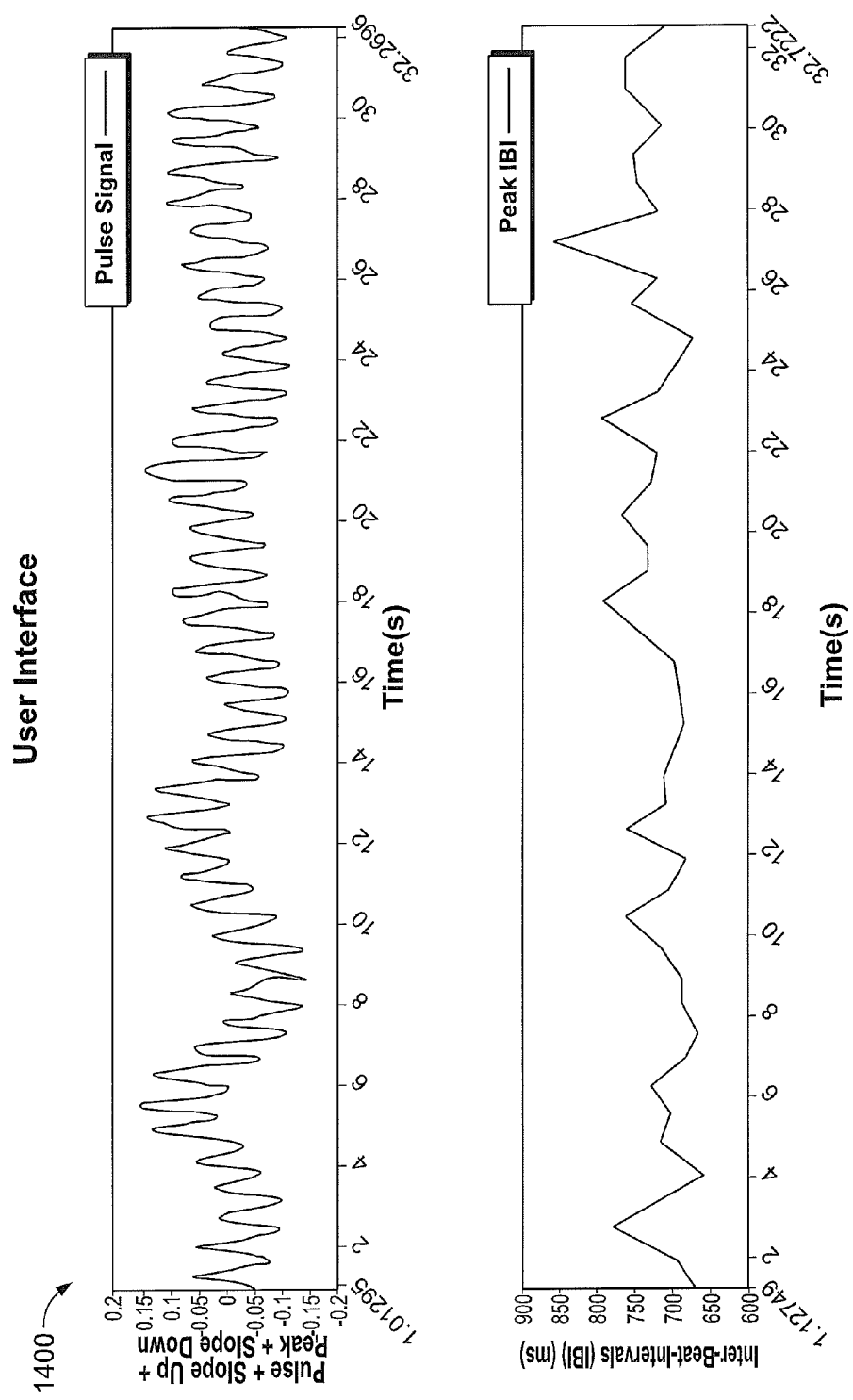
FIG. 14 illustrates exemplary embodiments of the user interfaces showing the display of information obtained through the use of the present invention

FIG. 14 illustrates some of the different display screens that may be generated by certain embodiments of the present invention to communicate the use of and results obtained. 1400 illustrates the Clean Arterial Pulse 319 or 511 and the extracted parameter, which in one embodiment is the inter pulse interval time from 1300.

Figure 15:
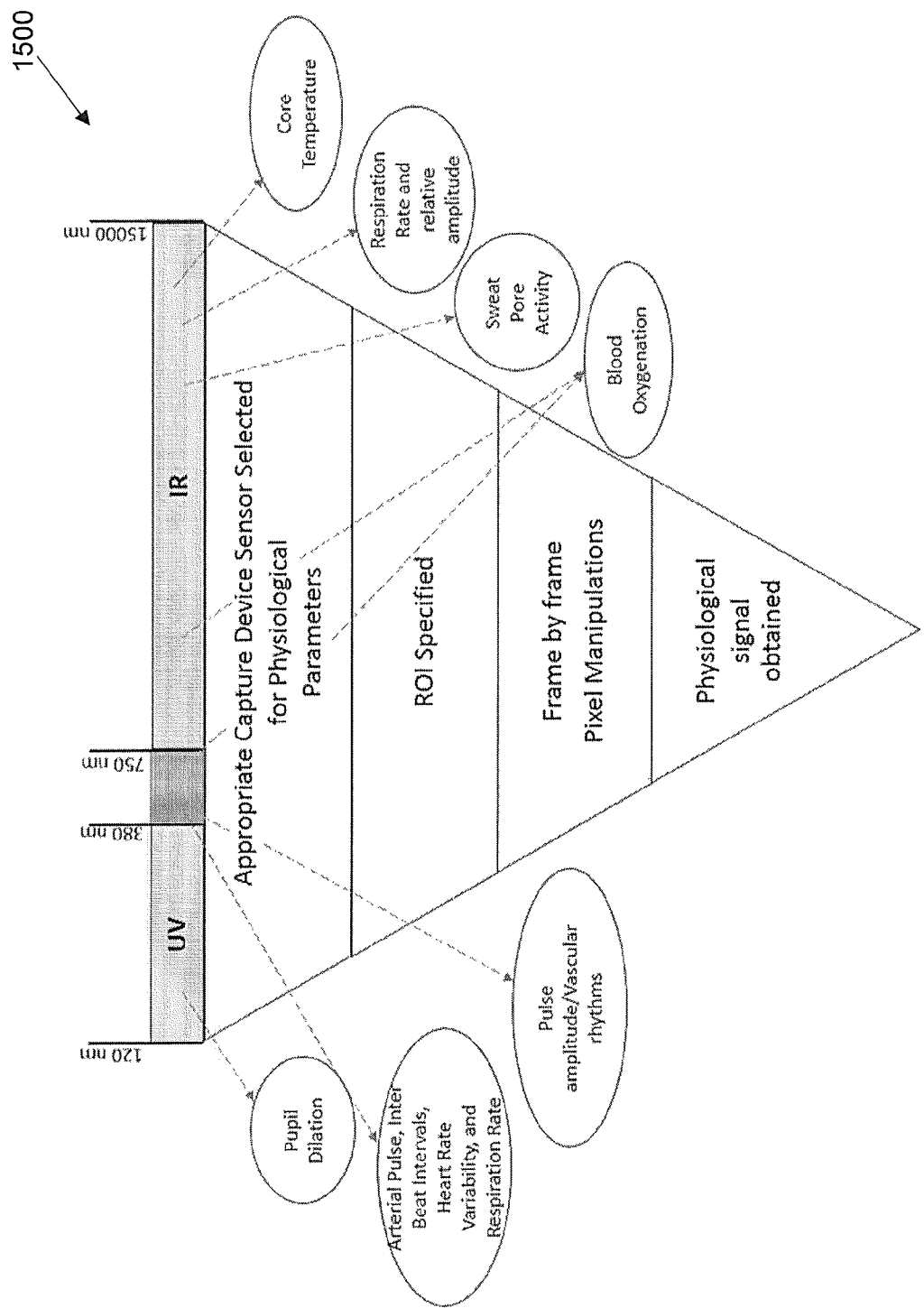
FIG. 15 is a diagram illustrating the physiological parameters that may be investigated through the use of the present invention.

FIG. 15 shows the application of the invention to a broad range of physiological signal acquisitions. In certain embodiments, hardware components may be used to accomplish a range of applications. Pulse rate extraction is one of many embodiments of the concept. In that embodiment, method 501, the contribution of changing light intensity to the extracted pulse wave is reduced. The D1-to-A-to-D2 approach is configurable to other sensor components or applications with color video cameras that are appropriate for the selected physiological signals. In one embodiment, pulse amplitude is derived from the filtered pulse wave 511. In one embodiment the RMS value of the filtered pulse wave is calculated and continuously shown. In another embodiment an envelope function of the same is applied to the filtered pulse wave.

In a different embodiment of the D1-to-A-to-D2 algorithm, pupil dilation is measured with an imaging sensor sensitive to near infrared wavelengths of light. Edge enhancement sharpens the pupil/iris boundary with pixel level preprocessing 406, pattern matching tracks the changing circle diameter of the pupil, creating the "A" or analog signal representing changing pupil diameter.

In another embodiment shown in 1500, Oxygen Saturation is measured by a custom designed sensor including an array of two narrow wavelength sensors. One may be sensitive to 660 nm and one to 940 nm. The camera mount may include a reflective region that directs a portion of the overhead light directly to the sensor. The remainder of the pixels may then be focused on the subject's face. The camera may take a single, long exposure (3 second) image, then calculates the ratio of the two wavelengths reflected off the skin (correcting for the ambient levels detected from the overhead lights). This ratio provides a quantitative measure of oxygen perfusion, a critical vital sign in several conditions (e.g., infection).

In yet another embodiment, Sweat Pore activity may be monitored by a Medium wavelength infrared imaging sensor. Edge enhanced images 406 from each frame may be used to generate entropy level calculations within an ROI that encompasses an area of the skin with visible sweat pores. Change in Entropy (i.e., pattern on the skin) correlates with pore openings due to sweat pore response and is the underlying analog physiological signal monitored.

In another embodiment of the algorithm, Respiration Rate and Amplitude are the signals of interest. The sensor is a Medium wavelength infrared sensor. The ROI is placed on the bottom of the nose. Mean Temperature is tracked within the ROI. Series of values are integrated (since temperature correlates with flow, or changing volume over time) to create a measure of lung volume at each moment.

In a final embodiment, core body temperature is measured from a medium wavelength thermal imaging sensor. A ROI based on contextual information. Camera includes thermal calibration information to translate a pixel intensity to a temperature. A geometric mask is applied, then average intensity across a selected region is tracked for a short period of time. Core temperature is derived from this average.

Figure 16:
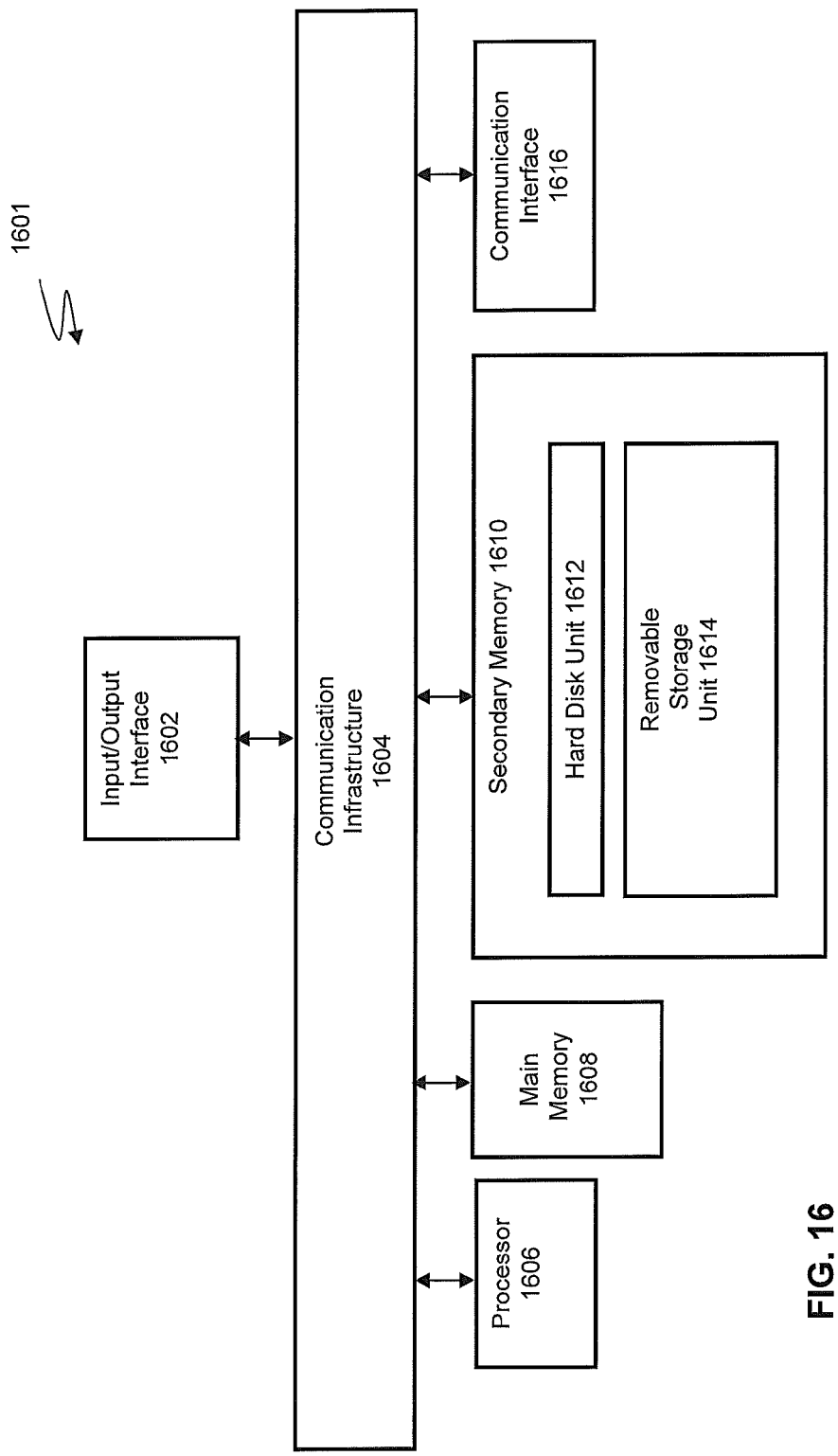
FIG. 16 is a schematic view of a computing system according to one preferred embodiment of the present invention.

FIG. 16 illustrates an exemplary computer system 1601 that may be used to implement the methods according to the invention. Computer system 1601 includes an input/output interface 1602 connected to communication infrastructure 1604—such as a bus—, which forwards data such as graphics, text, and information, from the communication infrastructure 1604 or from a frame buffer (not shown) to other components of the computer system 1601. The input/output interface 1602 may be, for example, a display device, a keyboard, touch screen, joystick, trackball, mouse, monitor, speaker, printer, Google Glass® unit, web camera, any other computer peripheral device, or any combination thereof, capable of entering and/or viewing data.

Computer system 1601 includes one or more processors 606, which may be a special purpose or a general-purpose digital signal processor configured to process certain information. Computer system 1601 also includes a main memory 608, for example random access memory (RAM), read-only memory (ROM), mass storage device, or any combination thereof. Computer system 1601 may also include a secondary memory 1610 such as a hard disk unit 1612, a removable storage unit 1614, or any combination thereof. Computer system 1601 may also include a communication interface 1616, for example, a modem, a network interface (such as an Ethernet card or Ethernet cable), a communication port, a PCMCIA slot and card, wired or wireless systems (such as Wi-Fi, Bluetooth, Infrared), local area networks, wide area networks, intranets, etc.

It is contemplated that the main memory 1608, secondary memory 1610, communication interface 1616, or a combination thereof, function as a computer usable storage medium, otherwise referred to as a computer readable storage medium, to store and/or access computer software including computer instructions. For example, computer programs or other instructions may be loaded into the computer system 1601 such as through a removable storage device, for example, a floppy disk, ZIP disks, magnetic tape, portable flash drive, optical disk such as a CD or DVD or Blu-ray, Micro-Electro-Mechanical Systems (MEMS), nanotechnological apparatus. Specifically, computer software including computer instructions may be transferred from the removable storage unit 1614 or hard disc unit 1612 to the secondary memory 1610 or through the communication infrastructure 1604 to the main memory 1608 of the computer system 1601.

Communication interface 1616 allows software, instructions and data to be transferred between the computer system 1601 and external devices or external networks. Software, instructions, and/or data transferred by the communication interface 1616 are typically in the form of signals that may be electronic, electromagnetic, optical or other signals capable of being sent and received by the communication interface 1616. Signals may be sent and received using wire or cable, fiber optics, a phone line, a cellular phone link, a Radio Frequency (RF) link, wireless link, or other communication channels.

Computer programs, when executed, enable the computer system 1601, particularly the processor 1606, to implement the methods of the invention according to computer software including instructions.

The computer system 1601 described may perform any one of, or any combination of, the steps of any of the methods according to the invention. It is also contemplated that the methods according to the invention may be performed automatically.

The computer system 1601 of FIG. 16 is provided only for purposes of illustration, such that the invention is not limited to this specific embodiment. It is appreciated that a person skilled in the relevant art knows how to program and implement the invention using any computer system.

The computer system 1601 may be a handheld device and include any small-sized computer device including, for example, a personal digital assistant (PDA), smart hand-held computing device, cellular telephone, or a laptop or netbook computer, hand held console or MP3 player, tablet, or similar hand held computer device, such as an iPad®, iPad Touch® or iPhone®.

Figure 17:
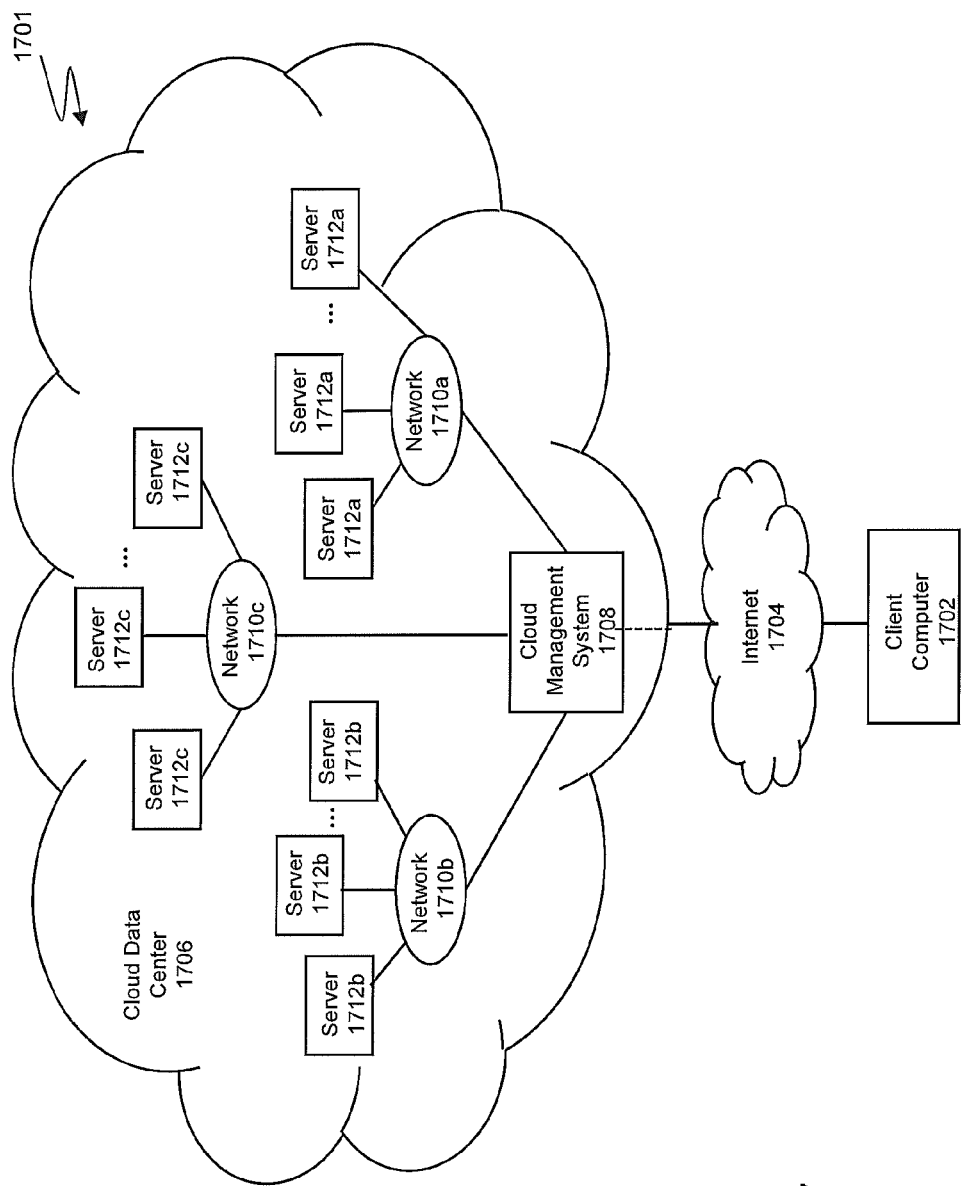
FIG. 17 is a schematic view of an exemplary cloud computing system according to one preferred embodiment of the present invention.

FIG. 17 illustrates an exemplary cloud computing system 1701 that may be used to implement the methods according to the present invention. The cloud computing system 701 includes a plurality of interconnected computing environments. The cloud computing system 1701 utilizes the resources from various networks as a collective virtual computer, where the services and applications can run independently from a particular computer or server configuration making hardware less important.

Specifically, the cloud computing system 1701 includes at least one client computer 702. The client computer 1702 may be any device through the use of which a distributed computing environment may be accessed to perform the methods disclosed herein, for example, a traditional computer, portable computer, mobile phone, personal digital assistant, tablet to name a few. The client computer 02 includes memory such as random access memory (RAM), read-only memory (ROM), mass storage device, or any combination thereof. The memory functions as a computer usable storage medium, otherwise referred to as a computer readable storage medium, to store and/or access computer software and/or instructions.

The client computer 702 also includes a communications interface, for example, a modem, a network interface (such as an Ethernet card), a communications port, a PCMCIA slot and card, wired or wireless systems, etc. The communications interface allows communication through transferred signals between the client computer 702 and external devices including networks such as the Internet 704 and cloud data center 706. Communication may be implemented using wireless or wired capability such as cable, fiber optics, a phone line, a cellular phone link, radio waves or other communication channels.

The client computer 702 establishes communication with the Internet 704—specifically to one or more servers—to, in turn, establish communication with one or more cloud data centers 706. A cloud data center 706 includes one or more networks 710a, 710b, 710c managed through a cloud management system 708. Each network 710a, 710b, 710c includes resource servers 712a, 712b, 712c, respectively. Servers 712a, 712b, 712c permit access to a collection of computing resources and components that can be invoked to instantiate a virtual machine, process, or other resource for a limited or defined duration. For example, one group of resource servers can host and serve an operating system or components thereof to deliver and instantiate a virtual machine. Another group of resource servers can accept requests to host computing cycles or processor time, to supply a defined level of processing power for a virtual machine. A further group of resource servers can host and serve applications to load on an instantiation of a virtual machine, such as an email client, a browser application, a messaging application, or other applications or software.

The cloud management system 708 can comprise a dedicated or centralized server and/or other software, hardware, and network tools to communicate with one or more networks 710a, 710b, 710c, such as the Internet or other public or private network, with all sets of resource servers 712a, 712b, 712c. The cloud management system 708 may be configured to query and identify the computing resources and components managed by the set of resource servers 712a, 712b, 712c needed and available for use in the cloud data center 706. Specifically, the cloud management system 708 may be configured to identify the hardware resources and components such as type and amount of processing power, type and amount of memory, type and amount of storage, type and amount of network bandwidth and the like, of the set of resource servers 712a, 712b, 712c needed and available for use in the cloud data center 706. Likewise, the cloud management system 708 can be configured to identify the software resources and components, such as type of Operating System (OS), application programs, and the like, of the set of resource servers 712a, 712b, 712c needed and available for use in the cloud data center 706.

The present invention is also directed to computer products, otherwise referred to as computer program products, to provide software to the cloud computing system 701. Computer products store software on any computer useable medium, known now or in the future. Such software, when executed, may implement the methods according to certain embodiments of the invention. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems (MEMS), nanotechnological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

The cloud computing system 701 of FIG. 7 is provided only for purposes of illustration and does not limit the invention to this specific embodiment. It is appreciated that a person skilled in the relevant art knows how to program and implement the invention using any computer system or network architecture.

It should be noted that various changes and modifications to the presently preferred embodiments described herein will be apparent to those skilled in the art. Such changes and modifications may be made without departing from the spirit and scope of the present invention and without diminishing its attendant advantages.

What is claimed is:

1. A computer method for determining one or more physiological parameters of a living subject comprising:
    capturing by a capture device at least two images having a temporally sequential relationship of a region of interest (ROI) on a body surface of the living subject and generate digital signals for each of the at least two images as digital output;
    a processing component processing the digital output for each of the at least two images comprising the steps of:
    (a) capturing by the processing component the each of the at least two images as information on an analog-to-digital sensor that has been calibrated by the processing component, based upon the one or more physiological parameters, environmental context in which the living subject is positioned, and specifications of the capture device, to adjust information content in the digital output;
    (b) receiving by the processing component and preprocessing the digital output from the each of the at least two images in real-time to select the ROI in the each of the at least two images individually;
    (c) extracting by the processing component a pulse wave sample from the ROI for the each of the at least two images, the extracted pulse wave sample corresponding to a single time point represented by the each of the at least two images, the preprocessing including separating the digital output into red light data, green light data, and blue light data and calculating a ratio of red light data to green light data;
    (d) combining by the processing component multiple color planes information, including at least one of hue, saturation, luminance, intensity, and value, with the red light, green light, and blue light data to modify the extracted pulse wave sample;
    (e) generating by the processing component a second pulse wave sample by step (a), step (b), step (c) and step (d), or any subset thereof for the each of the at least two images:
    (f) post-processing by the processing component the second pulse wave sample of step (e) to form a post-processed pulse wave; and
    (g) determining by the processing component the physiological parameter of the subject from the post-processed pulse wave of step (f).

2. The computer method of claim 1 wherein the preprocessing includes at least one of masking to remove non-skin pixels and correcting for movement of the subject.

3. The computer method of claim 2, wherein the correcting for movement comprises using a ratio-based measure.

4. The computer method of claim 2, wherein the correcting for movement employs a pixel level correction, comprising:
   (a) a series of one or more mathematical operations combining information from two or more color plane values for a given pixel;
   (b) a series of one or more mathematical operations combining information from two or more adjacent pixels within a color plane; or
   (c) any combination of procedures (a) or (b).

5. The computer method of claim 2, wherein the masking is accomplished by creating a specific skin mask designed using a profile of the body surface based on hue, saturation, and/or luminance of the body surface and applying the skin mask to the each of the at least two images to remove non-skin pixels.

6. The computer method of claim 1, wherein the pre-processing includes pixel level correction to minimize impact of lighting.

7. The computer method of claim 1, wherein the post-processing comprises one or more of filtering, performing time series analysis, detrending, and curve fitting.

8. The computer method of claim 1, wherein the processing component extracts interbeat intervals from the arterial pulse wave.

9. The computer method of claim 8, wherein the processing component extracts from the interbeat intervals components of heart rate variability, including at least one of low frequency and respiratory sinus arrhythmia.

10. The computer method of claim 8, wherein the processing component extracts a respiration rate from the interbeat intervals.

11. A method for measuring physiological parameters of a human subject, the method comprising:
   (a) capturing a temporal sequence of images from which a region of interest (ROI) identifiable on a body surface on the subject using a digital color video;
   (b) preprocessing in real time the ROI in the each of the images individually, to extract a pulse signal from the ROI for the each of the images, each of the pulse signals corresponding to a single time point, said pre-processing including separating light into red, green, and blue light and calculating a ratio of red to green light;
   (c) generating in real-time a pulse wave from the pulse signals obtained through step (b) for the each of the images;
   (d) post-processing the pulse wave generated by step (c) to provide a post-processed pulse wave for the each of the images; and
   (e) determining arterial blood pulse rate and amplitude of the subject from the post-processed pulse wave of step (d) for the each of the images.

12. The method of claim 11, wherein the body surface comprises a high capillary density.

13. The method of claim 11, wherein the pre-processing includes at least one of masking to remove non-skin pixels and correcting for movement of the skin surface.

14. The method of claim 13, wherein the correcting for movement comprises employing a ratio-based measure.

15. The method of claim 13, wherein said correcting for movement employs a pixel level correction.

16. The method of claim 11, wherein the pre-processing includes pixel level correction to minimize impact of lighting.

17. The method of claim 11, wherein the post-processing comprises one or more of filtering, performing time series analysis, detrending, and curve fitting.

18. The method of claim 11, further comprising extracting interbeat intervals from the pulse wave.

19. The method of claim 18, further comprising extracting from the interbeat intervals components of heart rate variability selected from low frequency and respiratory sinus arrhythmia.

20. The method of claim 18, further comprising extracting respiration rate from the interbeat intervals.

21. The method of claim 18, further comprising extracting beat to beat pulse amplitude.

22. A method for evaluating a human subject for stress response, the method comprising:
   monitoring a physiological response of the subject according to claim 11;
   exposing the subject to a challenge while continuing to monitor the physiological response; and
   evaluating the physiological response before and after the challenge.

23. A computer method for determining one or more physiological parameters of a living subject comprising:
   a capture device to capture images consisting of a first single image and a second single image having a temporally sequential relationship of a region of interest (ROI) on a body surface of the living subject and generate digital signals of the first single image and the second single image as digital output;
   a processing component processing the digital output comprising the steps of:
   (a) capturing by said processing component each of the first single image and the second single image as information on an analog-to-digital sensor that has been calibrated by said processing component, based upon the one or more physiological parameters, environmental context in which the living subject is positioned, and specifications of the capture device, to adjust information content in the digital output;
   (b) receiving by said processing component and pre-processing the digital output from the each of the first single image and the second single image in real-time to select the ROI in the each of the at least two images individually;
   (c) extracting by said processing component a pulse wave sample from the ROI for the each of the first single image and the second single image, the extracted pulse wave sample corresponding to a single time point represented by the each of the first single image and the second single image, the preprocessing including separating the digital output into red light data, green light data, and blue light data and calculating a ratio of red light data to green light data;
   (d) combining by said processing component multiple color planes information, including at least one of hue, saturation, luminance, intensity, and value, with the red light, green light, and blue light data to modify the extracted pulse wave sample;
   (e) generating by said processing component a second pulse wave sample by step (a), step (b), step (c) and step (d), or any subset thereof for the each of the first single image and the second single image;
   (f) post-processing by said processing component the second pulse wave sample of step (e) to form a post-processed pulse wave; and (g) determining by said processor the physiological parameter of the subject from the post-processed pulse wave of step (f).

\* \* \* \* \*

UNITED STATES PATENT AND TRADEMARK OFFICE
CERTIFICATE OF CORRECTION

PATENT NO. : 10,004,410 B2  
APPLICATION NO. : 15/105674  
DATED : June 26, 2018  
INVENTOR(S) : Stephen W. Porges, Maria I. Davila and Gregory F. Lewis Page 1 of 1

It is certified that error appears in the above-identified patent and that said Letters Patent is hereby corrected as shown below:

In the Specification

Column 1, Line 9, before the heading "FIELD OF THE INVENTION", insert:
-- STATEMENT REGARDING FEDERALLY SPONSORED RESEARCH OR DEVELOPMENT
This invention was made with government support under grant no. W911NF-14-1-0158 awarded by ARMY/ARO. The government has certain rights in this invention. --

Signed and Sealed this
Second Day of April, 2019

Andrei Iancu
*Director of the United States Patent and Trademark Office*